United States Patent
Inoue et al.

(10) Patent No.: US 9,097,727 B2
(45) Date of Patent: Aug. 4, 2015

(54) METHOD FOR DIAGNOSING A PROTEIN MISFOLDING DISEASE USING NERVE CELLS DERIVED FROM IPS CELLS

(75) Inventors: Haruhisa Inoue, Kyoto (JP); Shiho Kitaoka, Kyoto (JP); Naoki Yahata, Kyoto (JP); Nobuhisa Iwata, Wako (JP); Takaomi Saido, Wako (JP)

(73) Assignees: KYOTO UNIVERSITY, Kyoto (JP); RIKEN, Saitama (JP)

( * ) Notice: Subject to any disclaimer, the term of this patent is extended or adjusted under 35 U.S.C. 154(b) by 164 days.

(21) Appl. No.: 13/582,403

(22) PCT Filed: Mar. 3, 2011

(86) PCT No.: PCT/JP2011/055570
§ 371 (c)(1),
(2), (4) Date: Oct. 24, 2012

(87) PCT Pub. No.: WO2011/108766
PCT Pub. Date: Sep. 9, 2011

(65) Prior Publication Data
US 2013/0034858 A1 Feb. 7, 2013

Related U.S. Application Data

(60) Provisional application No. 61/309,927, filed on Mar. 3, 2010.

(51) Int. Cl.
| | |
|---|---|
| G01N 33/48 | (2006.01) |
| G01N 33/50 | (2006.01) |
| G01N 33/573 | (2006.01) |
| G01N 33/68 | (2006.01) |
| C12N 5/0793 | (2010.01) |

(52) U.S. Cl.
CPC .......... *G01N 33/6896* (2013.01); *C12N 5/0619* (2013.01); *C12N 2501/11* (2013.01); *C12N 2501/115* (2013.01); *C12N 2501/13* (2013.01); *C12N 2501/155* (2013.01); *C12N 2501/385* (2013.01); *C12N 2501/41* (2013.01); *C12N 2501/91* (2013.01); *C12N 2503/02* (2013.01); *C12N 2506/00* (2013.01); *C12N 2506/45* (2013.01); *C12N 2533/32* (2013.01); *G01N 2333/4709* (2013.01); *G01N 2333/96486* (2013.01); *G01N 2800/2821* (2013.01)

(58) Field of Classification Search
None
See application file for complete search history.

(56) References Cited

U.S. PATENT DOCUMENTS

2009/0298775 A1  12/2009  Saido et al.

FOREIGN PATENT DOCUMENTS

| WO | WO 03/091449 A1 | 11/2003 |
|---|---|---|
| WO | WO 2004/081172 A1 | 9/2004 |
| WO | WO 2010/008486 A2 | 1/2010 |

OTHER PUBLICATIONS

Dimos et al., Science, 321(5893):1218-21,Epub Jul. 31, 2008.*
Wang et al., J Neurochem, 109(4):1072-1082, 2009.*
Park et al., Cell, 134(5):877-886, 2008.*
Nasonkin et al., Experimental Neurology, 201(2): 525-529, Oct. 2006.*
Abe, Y., et al., Analysis of Neurons Created From Wild-Type and Alzheimer's Mutation Knock-in Embryonic Stem Cells by a Highly Efficient Differentiation Protocol, J. Neurosci. 23(24):8513-8525, 2003.
Chamberlain, S.J., et al., Induced Pluripotent Stem (iPS) Cells as in Vitro Models of Human Neurogenetic Disorders, Neurogenetics 9(4):227-235, 2008.
Chambers, S.M., et al., Highly Efficient Neural Conversion of Human ES and iPS Cells by Dual Inhibition of SMAD Signaling, Nat. Biotechnol. 27(3):275-280, 2009.
Dimos, J.T., et al., Inducted Pluripotent Stem Cells Generated from Patients with ALS Can be Differentiated into Motor Neurons, Science, vol. 321, Aug. 29, 2008, pp. 1218-1221.
International Search Report dated Jun. 6, 2011, issued in connection with PCT/JP2011/055570.
Kahle, P.J., et al., Attack on Amyloid, International Titsee Conference on Alzheimer's and Parkinson's Disease: From Basic Science to Therapeutic Treatment, EMBO Reports 4(8):747-751, 2003.
Takahashi, K., et al., Induction of Pluripotent Stem Cells from Adult Human Fibroblasts by Defined Factors, Cell, vol. 131, Nov. 2007, pp. 861-872.
Wada, T., et al., Highly Efficient Differentiation and Enrichment of Spinal Motor Neurons Derived From Human and Monkey Embryonic Stem Cells, PLOS One 4(8):e6722, 2009.
D'Amour et al., "Production of pancreatic hormone—expressing endocrine cells from human embryonic stem cells," *Nature Biotechnology*, vol. 24(11), pp. 1392-1401 (Nov. 2006).
Okano, H., "iPS Saibou Wo Mochiita Shinkei Saisei Senryaku," *Geriatric Medicine*, vol. 47(10), pp. 1369-1377 (Oct. 2009).
Takahashi, K., et al., "Induction of Pluripotent Stem Cells from Adult Human Fibroblasts by Defined Factors," *Cell*, vol. 131, pp. 861-872 (Nov. 30, 2007).
Nakagawa, M., et al., Generation of Induced Pluripotent Stem Cells Without Myc From Mouse and Human Fibroblasts, Nat. Biotechnol. 26(1):101-106 (Jan. 2008).

* cited by examiner

*Primary Examiner* — Daniel E Kolker
*Assistant Examiner* — Stacey N MacFarlane
(74) *Attorney, Agent, or Firm* — Knobbe, Martens, Olson & Bear, LLP

(57) ABSTRACT

The present invention provides a method for detecting onset of, or the risk of development of, a protein misfolding disease, and a method for predicting the age of onset of a protein misfolding disease using nerve cells derived from iPS cells. The present invention also provides a kit to be used in these methods.

6 Claims, 9 Drawing Sheets

Fig. 4
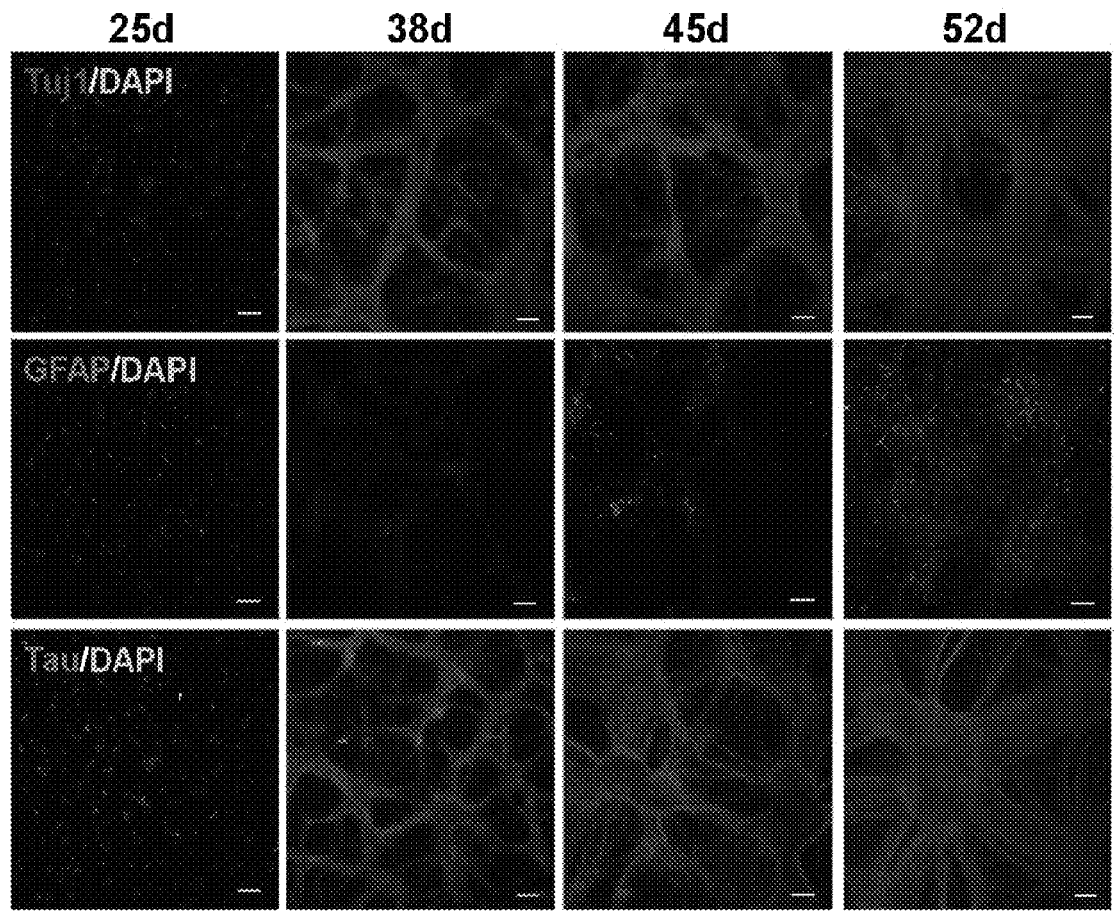
[Fig. 5]
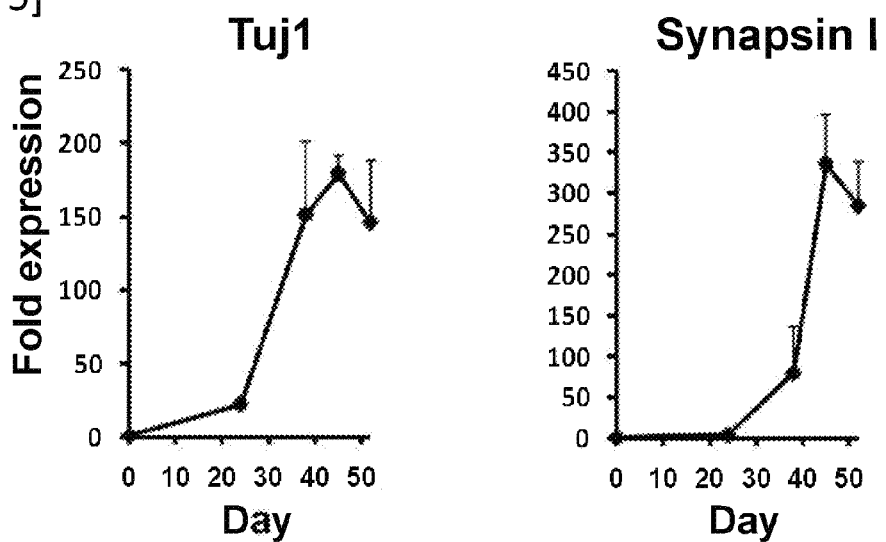

METHOD FOR DIAGNOSING A PROTEIN MISFOLDING DISEASE USING NERVE CELLS DERIVED FROM IPS CELLS

REFERENCE TO SEQUENCE LISTING

This application incorporates by reference the sequence listing submitted as ASCII text filed via EFS-Web on Aug. 31, 2012. The Sequence Listing is provided as a file entitled "TOYA204_001APC_SL.TXT", created on Aug. 31, 2012 and which is approximately 5 kilobytes in size.

TECHNICAL FIELD

The present invention relates to a method for diagnosing the onset of a protein misfolding disease and a risk of development thereof, which method uses nerve cells derived from induced pluripotent stem (iPS) cells, and to a kit to be used in this method. The present invention further relates to a method for prediction of the age of the onset of a protein misfolding disease and a kit to be used in this method.

BACKGROUND ART

Protein misfolding diseases are known as neurodegenerative diseases caused by cytotoxicity due to abnormally aggregated proteins (misfolded proteins) (1). Alzheimer's disease is a representative protein misfolding disease, which causes deposition of the amyloid β-protein (Aβ) outside nerve cells in brain. Since initiation of therapy as early as possible leads to effective therapy of Alzheimer's disease, development of a method of early diagnosis of the disease is an important task in an aging society.

At present, NINCDS-ADRDA and DSM-IV, which are excellent for diagnosis of positivity of Alzheimer's disease, are employed as clinical diagnostic criteria, but with these criteria, the possibility that a patient is diagnosed as negative for the disease at an early stage of onset cannot be eliminated. Needless to say, it is impossible to give a diagnosis before onset.

It has been revealed that Alzheimer's disease is caused by accumulation of Aβ, and there have been reports wherein decrease in the Aβ42/Aβ40 ratio and increase in phosphorylated tau (p-tau) protein in the cerebrospinal fluid, and their combination p-tau/(Aβ42/Aβ40), were used as diagnostic indices. However, nerve cell death has already been progressed in the period wherein these values as diagnostic indices increase. Therefore, even with these indices, early diagnosis and prediction of onset of Alzheimer's disease are difficult.

On the other hand, recently, it has been revealed that neprilysin functions as a protease that degrades Aβ in brain (2), and it has been reported that early accumulation of Aβ oligomers in brain as well as cognitive dysfunction occur in neprilysin-deficient model mice for Alzheimer's disease (3 and 4).

Further, it has been reported that, in Alzheimer's disease patients, expression of neprilysin is decreased in hippocampus and temporal lobe gyri, wherein senile plaques are observed, so that the relationship between neprilysin and Alzheimer's disease has been suggested also in human (5).

On the other hand, in the fields of regenerative medicine and the like, a technology that enables conversion of a cell convenient as a biomaterial into a cell of a desired type is demanded, and recently, mouse and human iPS cells were established in succession. Yamanaka et al. introduced four genes, that is, Oct3/4, Sox2, Klf4 and c-Myc, into human skin-derived fibroblasts and succeeded in establishment of iPS cells (6 and 7). Since iPS cells that are obtained in such a process may be produced using cells derived from a patient to be treated and then allowed to differentiate into cells of various tissues, they are considered to enable reproduction of the diseased state in vitro. In fact, by the above method, iPS cells derived from a patient suffering from amyotrophic lateral sclerosis, which is a neurodegenerative disease, were produced, and the cells were successfully induced to differentiate into nerve cells (8).

So far, however, there has been no report in which nerve cells derived from iPS cells are used to analyze expression and functional change of a molecule involved in development of a protein misfolding disease, especially Alzheimer's disease, and the diseased state is reproduced, thereby carrying out early diagnosis of Alzheimer's disease.

REFERENCES (1) Bucciantini M, et al., *Nature.* 416:507-511 (2002)
(2) Iwata, N, et al., *Nature Med.* 6:143-151 (2000)
(3) Iwata, N, et al., *Science.* 292:1550-1552 (2001)
(4) Huang, S. M. et al., *J. Biol. Chem.* 281:17941-17951 (2006)
(5) Yasojima K, et al., *Neuroscience Lett.* 297:97-100 (2001)
(6) WO 2007/069666 A1
(7) Takahashi, K. et al., *Cell.* 131:861-872 (2007)
(8) Dimos J T, et al., *Science.* 321:1218-21 (2008)

SUMMARY OF THE INVENTION

The present invention aims to diagnose the onset of a protein misfolding disease and a risk of development thereof, or to predict the age of the onset of a protein misfolding disease, using nerve cells derived from iPS cells produced from somatic cells of a protein misfolding disease patient. Therefore, the objects of the present invention are to provide a method for diagnosing the onset of and/or a risk of development of, a protein misfolding disease using cells derived from a test subject, and a kit used in the method; and to provide a method for predicting the age of the onset of a protein misfolding disease using cells derived from a test subject, and a kit using the method. In the present invention, the protein misfolding disease is preferably Alzheimer's disease.

The simplest way of diagnosis of a protein misfolding disease is to compare the amount of a causative protein or a function to degrade the protein (hereinafter referred to as the amount of a causative protein or the like) in a control subject where onset of the disease is known, with the amount of the causative protein or the like in the test subject. Since, in such a case, it is sometimes difficult to distinguish between progression of the disease condition and aging, it is necessary, for example, to compare a control subject whose onset of the disease is known with a test subject at the same age. However, since the amount of the protein at the desired age cannot be measured after confirming the onset of the disease, it is very difficult to preliminarily prepare data set showing the amounts of the causative protein or the like at the respective ages over a wide range of ages in a control subject whose onset of the disease is known. Further, in order to predict the age of the onset of the disease, the amount of the causative protein or the like needs to be preliminarily measured at the same age as the test subject in control subjects with a wide range of ages of onset, and, needless to say, it is difficult.

Further, since the area mainly affected by protein misfolding diseases is nerve cells, measurement of the amount of the causative protein or the like is preferably carried out for nerve cells. Because biopsy of nerve cells imposes a heavy burden to a living body, preliminary preparation of control subjects at the respective ages for diagnosis of a protein misfolding disease is problematic from an ethical point of view.

Since iPS cells can differentiate into any tissue by returning them to a blastocyst, they have properties similar to those of cells at an early stage of development. Therefore, nerve cells induced from iPS cells are considered, irrespective of the age of the individual from whom the somatic cells were obtained, to be in the state of nerve cells at a certain age of the individual. Thus, by comparing nerve cells obtained from iPS cells under the same conditions including differentiation induction, days of culture and the like, individual differences in nerve cells at an identical age among the individuals from whom the cells were obtained can be known.

In order to solve the above objects, the inventors of the present invention focused attention on Alzheimer's disease as an example of protein misfolding diseases, and established iPS cells from somatic cells derived from a test subject. Nerve cells were obtained by differentiation induction of the iPS cells, and the content of Aβ in the culture supernatant of the obtained nerve cells was measured. Also, the inventors of the present invention focused on activity of neprilysin, which degrades Aβ, and the activity of neprilysin in the cell lysate was measured. As a result, it was confirmed that these indices of Alzheimer's disease can be measured also in nerve cells produced by differentiation induction of the iPS cells.

From the above results, the inventors of the present invention discovered that the onset of, or the risk of development of, Alzheimer's disease can be diagnosed by using nerve cells produced by differentiation induction of iPS cells derived from a test subject to measure the amount of Aβ or the activity or the expression level of neprilysin, followed by comparing the obtained value with a measured value in such nerve cells from a control subject wherein the age of the onset of Alzheimer's disease is known. As another embodiment, the inventors of the present invention discovered that it is useful for prediction of the age of onset of Alzheimer's disease in a test subject to compare the amount of Aβ or an activity index or the expression level of neprilysin in cells derived from a control subject wherein the age onset of Alzheimer's disease is known with the amount of Aβ or the activity index or the expression level of neprilysin in nerve cells produced by differentiation induction of iPS cells derived from the test subject, thereby completed the present invention.

That is, the present invention is as follows.

[1] A method for diagnosing whether a test subject has developed a protein misfolding disease or whether a test subject has a risk of developing it, said method comprising the steps of:
 (a) establishing iPS cells from somatic cells derived from the test subject;
 (b) inducing differentiation of said iPS cells into nerve cells;
 (c) measuring the amount of a causative protein, or the activity or the expression level of an enzyme involved in degradation of the causative protein in said nerve cells; and
 (d) comparing said measured value with the amount of the causative protein in control cells, or with the activity or the expression level of the enzyme involved in degradation of the causative protein in control cells.

[2] The method according to [1], wherein said control cells are nerve cells obtained by differentiation induction of iPS cells produced from somatic cells derived from a control subject who has not developed the protein misfolding disease at the same age as the test subject, and when the amount of said causative protein in the test subject is higher than that in the control subject, or when the activity or the expression level of the enzyme involved in degradation of said causative protein in the test subject is lower than that in the control subject, it is indicated that the test subject has developed the protein misfolding disease or has a risk of developing it.

[3] The method according to [1], wherein said control cells are nerve cells obtained by differentiation induction of iPS cells produced from somatic cells derived from a control subject who has already developed the protein misfolding disease at the same age as the test subject, and when the amount of said causative protein in the test subject is higher than or equivalent to that in the control subject, or when the activity or the expression level of the enzyme involved in degradation of said causative protein in the test subject is lower than or equivalent to that in the control subject, it is indicated that the test subject has developed the protein misfolding disease or has a risk of developing it.

[4] The method according to [1], wherein said subject is human.

[5] The method according to [1], wherein said protein misfolding disease is Alzheimer's disease.

[6] The method according to [5], wherein said causative protein is amyloid β (Aβ).

[7] The method according to [6], wherein the amount of Aβ is the amount of Aβ40 or the amount of Aβ42, or the ratio of the amount of Aβ42 to that of Aβ40.

[8] The method according to [5], wherein the enzyme involved in degradation of said causative protein is neprilysin.

[9] The method according to [1], wherein said differentiation induction into nerve cells is differentiation induction accompanied by culturing with media contained B27-supplement and N2-supplement.

[10] A method for predicting the age of onset of a protein misfolding disease of a test subject, said method comprising the steps of:
 (a) establishing iPS cells from somatic cells derived from the test subject;
 (b) inducing differentiation of said iPS cells into nerve cells;
 (c) measuring the amount of a causative protein, or the activity or the expression level of an enzyme involved in degradation of a causative protein in said nerve cells; and wherein, when said measured value is equivalent to the amount of said causative protein or to the activity or the expression level of the enzyme involved in degradation of said causative protein in nerve cells obtained by differentiation induction of iPS cells produced from somatic cells of a control subject whose age of onset of the protein misfolding disease is known, it is indicated that the test subject develops the protein misfolding disease at the age when said control subject developed the protein misfolding disease.

[11] The method according to [10], wherein said subject is human.

[12] The method according to [10], wherein said protein misfolding disease is Alzheimer's disease.

[13] The method according to [12], wherein said causative protein is Aβ.

[14] The method according to [13], wherein the amount of said Aβ is the amount of Aβ40 or the amount of Aβ42, or the ratio of the amount of Aβ42 to that of Aβ40.

[15] The method according to [12], wherein the enzyme involved in degradation of said causative protein is neprilysin.

[16] The method according to [10], wherein said differentiation induction into nerve cells is differentiation induction accompanied by culturing with media contained B27-supplement and N2-supplement.

[17] A kit for diagnosing whether a test subject has developed a protein misfolding disease or whether a test subject has a risk of developing it, or for predicting the age of onset of a protein misfolding disease in a test subject, said kit comprising (a) a reprogramming substance(s) for production of iPS cells,
(b) a reagent(s) for differentiation induction into nerve cells, and
(c) a reagent for measurement of the amount of a causative protein or a reagent for measurement of the activity or the expression level of an enzyme involved in degradation of a causative protein.

[18] The kit according to [17], wherein said protein misfolding disease is Alzheimer's disease.

[19] The kit according to [17], wherein said reprogramming substance(s) comprise(s) at least one factor selected from the group consisting of the OCT family, MYC family, KLF family and SOX family.

[20] The kit according to [17], wherein said reagent(s) for differentiation induction into nerve cells comprise(s) at least one factor selected from the group consisting of BDNF, GDNF and neurotensin-3.

[21] The kit according to [18], wherein said causative protein is Aβ40 or Aβ42.

[22] The kit according to [18], wherein said enzyme involved in degradation of the causative protein is neprilysin.

[23] The kit according to [22], wherein said reagent for measurement of the activity of the enzyme involved in degradation of said causative protein contains a substrate of neprilysin.

[24] The kit according to [23], wherein said substrate of neprilysin is succinyl-alanyl-alanyl-phenylalanine-4-methylcoumarin-7-amide.

BRIEF DESCRIPTION OF THE DRAWING

FIG. 4 shows the image of immunostaining for Tuj1 (red), GFAP (green) and Tau (green) at 25, 38, 45, and 52 days after differentiation induction (photograph).

FIG. 5 shows the results of measurement of relative expression amount for Tuj1 and Synapsin mRNA in nerve cells derived from iPS cells (253G4) at each term. The value at 0 day after differentiation induction is used as standard.

DETAILED DESCRIPTION OF THE INVENTION

Figure 1:
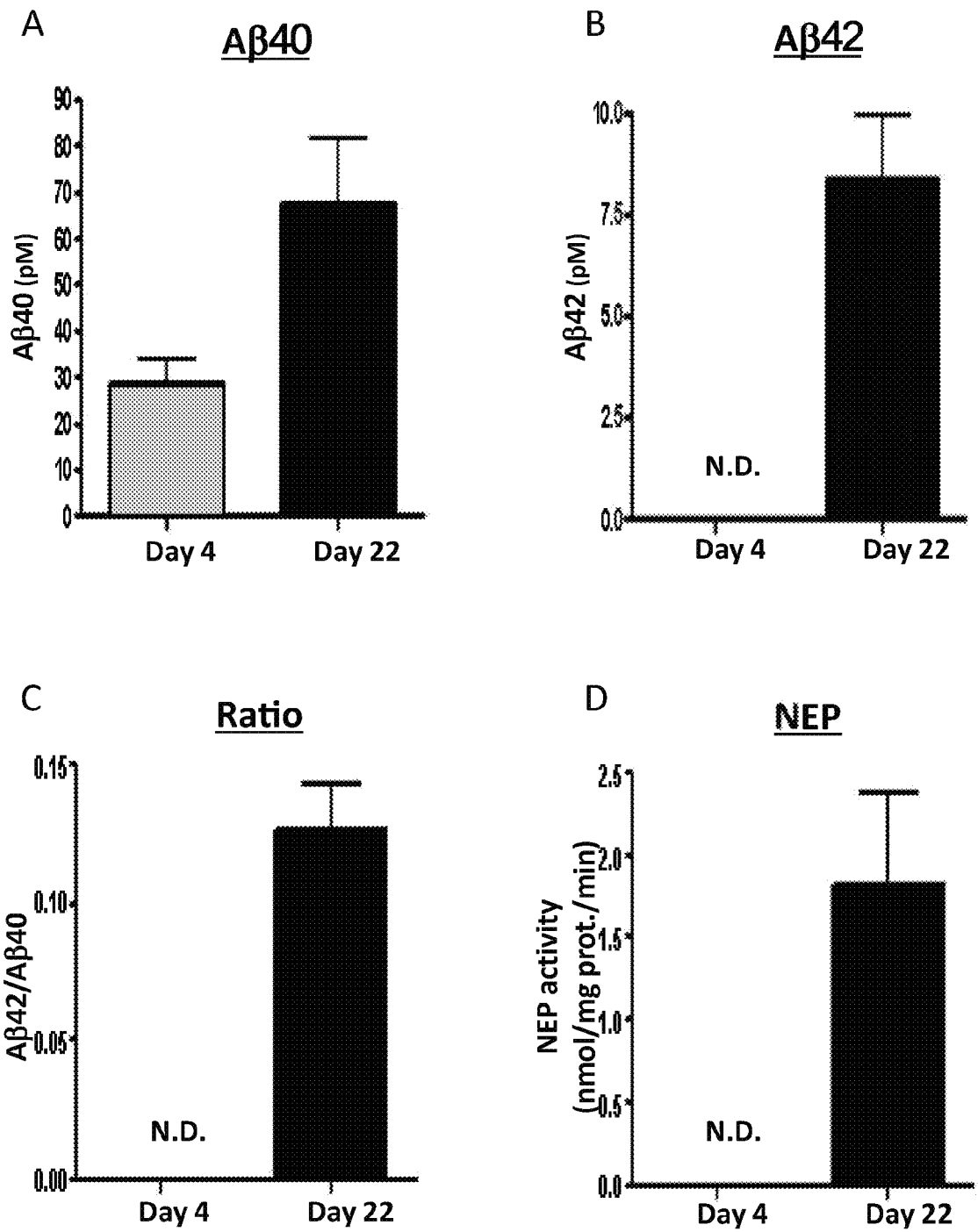
FIG. 1 shows the results of measurement of the contents of Aβ40 (A) and Aβ42 (B) in the culture supernatant of nerve cells derived from iPS cells, and the Aβ42/Aβ40 ratio (C). (D) shows the values obtained by measuring the neprilysin activity in iPS cell-derived nerve cells in the presence and absence of a neprilysin (NEP)-specific inhibitor thiorphan, thereby calculating the neprilysin-specific enzyme activity. The abscissa indicates the days after allowing the formed neurosphere to adhere to a culture dish and inducing its differentiation into nerve cells. In this figure, N.D. indicates that the obtained value was below the detection limit. Each experiment was carried out twice using 3 lots, and the mean±SE among the lots is shown.

The present invention provides a method for diagnosing whether a test subject has developed a protein misfolding disease or whether a test subject has a risk of developing it, the method comprising the steps of:

(a) establishing iPS cells from somatic cells derived from the test subject;

(b) inducing differentiation of the iPS cells into nerve cells;

(c) measuring the amount of a causative protein, or the activity or the expression level of an enzyme involved in degradation of a causative protein in the nerve cells; and (d) comparing the measured value with the amount of the causative protein in control cells, or with the activity value or the expression level of the enzyme involved in degradation of the causative protein in control cells.

The present invention also provides a method for predicting the age of the onset of a protein misfolding disease of a test subject, the method comprising the steps of:

(a) establishing iPS cells from somatic cells derived from the test subject;

(b) inducing differentiation of the iPS cells into nerve cells; and (c) measuring the amount of a causative protein, or the activity or the expression level of an enzyme involved in degradation of a causative protein in the nerve cells.

When the measured value is equivalent to the amount of the causative protein, or the activity or the expression level of the enzyme involved in degradation of the causative protein in nerve cells obtained by differentiation induction of iPS cells produced from somatic cells of a control subject whose age of onset of the protein misfolding disease is known, it is indicated that the test subject develops the protein misfolding disease at the age when the control subject developed the protein misfolding disease.

The present invention also provides a kit to be used for these methods.

In the present invention, the term "protein misfolding disease" means a group of diseases caused when a protein is not normally folded or the original structure of a protein is degenerated (misfolding). Examples of such a disease include, but are not limited to, diseases conventionally called neurodegenerative diseases such as Alzheimer's disease, Parkinson's disease, dementia with Lewy Bodies and multiple system atrophy.

In the present invention, the causative protein may be either a protein that is deposited outside the cells or a protein that accumulates inside the cells. In cases where the protein misfolding disease is Alzheimer's disease, examples of the causative protein include, but are not limited to, Aβ and tau. Similarly, in cases where the protein misfolding disease is Parkinson's disease, dementia with Lewy Bodies or multiple system atrophy, examples of the causative protein include, but are not limited to, α-synuclein.

In the present invention, the enzyme involved in degradation of the causative protein is preferably a protease. In cases where the causative protein is amyloid β, examples of the enzyme include, but are not limited to, neprilysin.

Details of the respective steps and the kit are as follows.

I. Production Method of iPS Cells

Induced pluripotent stem (iPS) cells can be produced by introducing certain specific nuclear reprogramming substances to somatic cells, which nuclear reprogramming substances may be in the forms of DNAs or proteins. iPS cells are somatic cell-derived artificial stem cells having properties almost equivalent to those of ES cells, such as pluripotency of differentiation and growth ability by self-renewal (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; WO 2007/069666). The nuclear reprogramming substances are not restricted as long as these are genes specifically expressed in ES cells, or genes playing important roles in maintenance of the undifferentiated state of ES cells, or gene products thereof. Examples of the nuclear reprogramming substances include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Nanog, Esrrb and Esrrg. These reprogramming substances may be used in combination when iPS cells are to be established. For example, the above reprogramming substance(s) may be used solely or as a combination of 2 or 3 reprogramming substances, preferably as a combination of 4 reprogramming substances.

The nucleotide sequences of the mouse and human cDNAs of the respective nuclear reprogramming substances described above, and the amino acid sequence information of the proteins encoded by the cDNAs can be obtained by reference to the NCBI accession numbers described in WO 2007/069666, and the mouse and human cDNA sequences and the amino acid sequence information of L-Myc, Lin28, Lin28b, Esrrb and Esrrg can be obtained by reference to the respective following NCBI accession numbers. Those skilled in the art can prepare a desired nuclear reprogramming substance based on the cDNA sequence or the amino acid sequence information, according to a conventional method.

| Gene name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

These nuclear reprogramming substances may be introduced into somatic cells in the form of proteins by a method such as lipofection, linking to a cell-permeable peptide, or microinjection. Alternatively, the nuclear reprogramming substances may be introduced into somatic cells in the form of DNAs by a method such as usage of a vector including virus, plasmid and artificial chromosome vectors; lipofection; usage of liposome; or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (Proc Jpn Acad Ser B Phys Biol Sci. 85, 348-62, 2009). Examples of the artificial chromosome vectors include human artificial chromosome (HAC), yeast artificial chromosome (YAC), and bacterial artificial chromosome (BAC, PAC). Examples of the plasmids which may be used include plasmids for mammalian cells (Science, 322: 949-953, 2008). The vectors may comprise a regulatory sequence(s) such as a promoter, enhancer, ribosome binding sequence, terminator and/or polyadenylation site in order to allow expression of the nuclear reprogramming substance(s); and, as required, a sequence of a selection marker such as a drug resistance gene (e.g., kanamycin-resistant gene, ampicillin-resistant gene or puromycin-resistant gene), thymidine kinase gene or diphtheria toxin gene; and a gene sequence of a reporter such as the green-fluorescent protein (GFP), β-glucuronidase (GUS) or FLAG. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. Further, the above vector may contain EBNA-1 and oriP, or Large T and SV40ori sequences.

For enhancing the induction efficiency of iPS cells upon the nuclear reprogramming, histone deacetylase (HDAC) inhibitors [for example, low molecular inhibitors such as valproic acid (VPA) (Nat. Biotechnol., 26(7): 795-797 (2008)), trichostatin A, sodium butyrate, MC1293 and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], Wnt Signaling (e.g., soluble Wnt3a) (Cell Stem Cell, 3, 132-135 (2008)), cytokines such as LIF an bFGF, ALKS inhibitors (e.g., SB431542) (Nat Methods, 6: 805-8 (2009)), mitogen-activated protein kinase signaling inhibitors, glycogen synthase kinase-3 inhibitors (PLoS Biology, 6(10), 2237-2247 (2008)), miRNAs such as miR-291-3p, miR-294 and miR-295 (R. L. Judson et al., Nat. Biotech., 27: 459-461 (2009)), and the like may be used in addition to the above-described factors.

Examples of the culture medium for induction of the iPS cells include (1) DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells, ReproCELL Inc., Kyoto, Japan).

Examples of the culture method include a method wherein somatic cells and nuclear reprogramming substances (DNAs or proteins) are brought into contact with each other at 37° C. in the presence of 5% $CO_2$ in DMEM or DMEM/F12 medium supplemented with 10% FBS, and the cells are cultured for about 4 to 7 days, followed by plating the cells on feeder cells (e.g., mitomycin C-treated STO cells, SNL cells or the like) and starting culture in a bFGF-containing culture medium for primate ES cells about 10 days after the contact between the somatic cells and the reprogramming substances, thereby allowing iPS-like colonies to appear about 30 to about 45 days after the contact, or later. To enhance the induction efficiency of iPS cells, the culture may be carried out under a condition wherein the concentration of oxygen is as low as 5 to 10%.

As an alternative culture method, the somatic cells may be cultured on feeder cells (e.g., mitomycin C-treated STO cells, SNL cells or the like) in DMEM medium supplemented with 10% FBS (which may further contain LIF, penicillin/streptomycin, puromycin, L-glutamine, non-essential amino acids, β-mercaptoethanol and/or the like, as appropriate), thereby allowing ES-like colonies to appear after about 25 to about 35 days of the culture, or later.

During the above culturing period, the culture medium is replaced with a fresh culture medium once every day from Day 2 of the culture. The number of the somatic cells used for nuclear reprogramming is not restricted, and usually within the range of about $5\times10^3$ to about $5\times10^6$ cells per 100-cm² area on the culture dish.

When a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present specification means any cells, excluding germ cells, derived from a mammal (e.g., human, mouse, monkey, pig or rat). Examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cells) or terminally-differentiated mature cells may be used as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

In the present invention, the mammalian subject from which the somatic cells are collected is not restricted, and preferably human. More preferably, the somatic cells are collected from a patient whose age of onset of the protein misfolding disease is known, and from a test subject.

II. Method of Differentiation Induction into Neural Stem Cells

In the present invention, "neural stem cells" means cells having an ability to differentiate into nerve cells, astrocytes and oligodendrocytes and capable of self-renewal. In the present invention, the term of "nerve cell" is not distinguished with the terms of "neuron" or "neural cell"

The method of differentiation induction of the above-mentioned iPS cells into neural stem cells is not restricted, and examples of the method which may be used include a differentiation induction method by high-density culture on a fibroblast feeder layer (JP 2008-201792 A), a differentiation induction method by co-culturing with stromal cells (SDIA method) (e.g., WO 2001/088100 and WO 2003/042384) and a differentiation induction method by suspension culture (SFEB method) (WO 2005/123902), and methods by combination of these methods.

As another embodiment, the differentiation induction may be carried out by forming a neurosphere by suspension culture. Preferred examples of the method include a method wherein the cells to be used for the suspension culture is prepared by adherent culture on a culture dish preliminarily subjected to coating treatment, which contains an arbitrary medium.

As another embodiment, the differentiation induction may be carried out by adhesion culture using coated dish to substitute for feeder cells.

Examples of the coating agent to be used in the adherent culture before the formation of a neurosphere include collagen, gelatin, poly-L-lysine, poly-D-lysine, fibronectin, laminin, entactin, and collagen IV, and combinations thereof. The coating agent is preferably the combination of poly-L-lysine and laminin, or entactin, collagen IV and laminin. The combination of entactin, collagen IV and laminin can be purchased from Millipore as "ECL Cell Attachment Matrix"

The medium to be used may be prepared by adding an additive(s) to a basal medium. The basal medium is not restricted as long as it can be used for culture of animal cells, and examples thereof include Neurobasal medium, Neural Progenitor Basal medium, NS-A medium, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, DMEM/F12 medium, Ham's medium, RPMI 1640 medium and Fischer's medium, and mixed media thereof. The basal medium is more preferably a mixture of Neurobasal medium and DMEM/F12. Examples of the additive(s) include serum, retinoic acid, BMP inhibitors, TGFβ family inhibitors, bFGF, EGF, HGF, LIF, amino acids, vitamins, interleukins, insulin, transferrin, heparin, heparan sulfate, collagen, fibronectin, progesterone, selenite, B27-supplement, N2-supplement, ITS-supplement and antibiotics. Preferred additives are BMP inhibitor, glutamine as an amino acid, B27-supplement and N2-supplement.

In the present invention, BMP inhibitor involved in inhibition of the BMP signaling that is mediated by binding of BMP to a BMP receptor (type I or type II). Examples of a BMP inhibitor having such properties include a compound that inhibits BMP2, BMP4, BMP6 or BMP7 capable of activating a transcription factor SMAD1, SMAD5, or SMAD8, such as Noggin, chordin, follistatin, Dorsomorphin (that is, 6-[4-(2-piperidin-1-yl-ethoxy)phenyl]-3-pyridin-4-yl-pyrazolo[1,5-a]pyrimidine) and a derivative thereof (P. B. Yu et al. (2007), Circulation, 116: II_60; P. B. Yu et al. (2008), Nat. Chem. Biol., 4: 33-41; J. Hao et al. (2008), PLoS ONE (www.plozone.org), 3 (8): e2904), LDN-193189 (that is, 4-(6-(4-(piperazin-1-yl)phenyl)pyrazolo[1,5-a]pyrimidin-3-yl)quinoline) and a derivative thereof (Yu P B et al. Nat Med, 14: 1363-9, 2008). In this invention, preferable BMP inhibitor is Noggin.

In the present invention, TGFβ family inhibitor is a compound which interferes with the signaling of the TGFβ family. Examples of such TGFβ family inhibitor include SB431542, SB202190 (R. K. Lindemann et al., Mol. Cancer 2: 20 (2003)), SB505124 (GlaxoSmithKline), NPC30345, SD093, SD908, SD208 (Scios), LY2109761, LY364947, and LY580276 (Lilly Research Laboratories), and A-83-01 (WO 2009146408). SB431542 is preferred.

The concentration of the iPS cells at the beginning of the culture may be set appropriately to allow efficient formation of neural stem cells. The concentration of the iPS cells at the beginning of the culture is not restricted, and, for example, about $1 \times 10^3$ to about $1 \times 10^6$ cells/ml, preferably about $1 \times 10^4$ to about $5 \times 10^5$ cells/ml.

Other culture conditions such as the culture temperature and the $CO_2$ concentration may be set appropriately. The culture temperature is not restricted, and, for example, about 30 to 40° C., preferably about 37° C. The $CO_2$ concentration is, for example, about 1 to 10%, preferably about 5%.

The neurosphere may be formed by suspension culture using the above basal medium and additive(s). Preferred examples of the medium include a mixture of Neurobasal medium and DMEM/F12. Preferred examples of the additive(s) include serum, Noggin as a BMP inhibitor, bFGF, EGF, heparin, B27-supplement and N2-supplement The cell concentration at the beginning of formation of the neurosphere may be set appropriately to allow efficient formation of the neurosphere. The cell concentration at the beginning of the culture is not restricted, and, for example, about $1 \times 10^4$ to about $5 \times 10^6$ cells/ml, preferably about $5 \times 10^5$ to about $2 \times 10^6$ cells/ml.

In the formation of a neurosphere, the cells may be subcultured when the size of the neurosphere becomes appropriate. The days of formation of the neurosphere is not restricted, and preferably every 15 days to 45 days, more preferably every 30 days. For the subculture, the cells may not necessarily be completely separated from each other, and separation of the cells may be carried out either by a mechanical method or by using a separation solution having a protease activity and collagenase activity. The number of times of subculture is not restricted, and preferably not less than once. Preferably, the number of times of subculture is twice before differentiation induction into nerve cells.

In the formation of a neurosphere, the culture vessel is preferably non-cell-adhesive. As the non-cell-adhesive culture vessel, one that has not been artificially treated for the purpose of enhancement of adhesiveness to cells (e.g., not coated with an extracellular matrix or the like), or one that has been artificially treated such that adhesion of cells is suppressed (e.g., coated with polyhydroxyethyl methacrylate (poly-HEMA)).

Other culture conditions during the formation of a neurosphere, such as the temperature and the $CO_2$ concentration, may be set appropriately. The culture temperature is not restricted, and, for example, about 30 to 40° C., preferably about 37° C. The $CO_2$ concentration is, for example, about 1 to 10%, preferably about 5%.

In the case of adhesion culture without formation of a neurosphere, iPS cells may be used, whose size of the colony becomes appropriate. The above coating agent, basal medium and additive(s) are used for culture. Preferred examples of the medium include a mixture of Neurobasal medium and DMEM/F12. Preferred examples of the additive(s) include serum, Noggin as a BMP inhibitor, SB431542 as a TGFβ family inhibitor, B27-supplement and N2-supplement. The days of using Noggin and SB431542 as additive is not restricted, and preferably 10 days to 24 days, more preferably every 17 days. After that, the additives may be changed to B27-supplement and N2-supplement without Noggin and SB431542. The days of adhesion culture in total for inducing neural stem cells are preferably 15 days to 30 days, more preferably 24 days. The coating agent may be changed at passage. Preferable coating agent is poly-L-lysine and laminin at first. Then, coating agent may be changed to poly-L-lysine laminin, entactin, and collagen IV. The days of using poly-L-lysine and laminin as coating agents is not restricted, and preferably 7 days to 14 days, more preferably every 10 days, and the days of using poly-L-lysine laminin, entactin, and collagen IV as coating agents is not restricted, and preferably 4 days to 10 days, more preferably every 7 days.

The thus induced neural stem cells can be identified by intermediate filament proteins such as N-CAM, polysialylated N-CAM, A2B5, nestin and vimentin; and expression markers for primitive neuroectoderm and neural stem cells, such as a transcription factor Pax-6. The cells are preferably confirmed by expression of nestin.

III. Method of Differentiation Induction into Nerve Cells

The neural stem cells induced by the above-mentioned method can be induced to differentiate into nerve cells by separating the neural stem cells by an arbitrary method and culturing them on a culture dish subjected to coating treatment, which contains an arbitrary medium. The nerve cells are preferably cerebrocortical neurons.

Here, the separation of the cells may be carried out either by a mechanical method or by using a separation solution having a protease activity and collagenase activity (e.g., Accutase™ or Accumax™).

Examples of the coating agent include collagen, gelatin, poly-L-lysine, poly-D-lysine, fibronectin and laminin, and combinations thereof. The coating agent is preferably the combination of poly-L-lysine, fibronectin and laminin.

The medium to be used may be prepared by adding an additive(s) to a basal medium. The basal medium is not restricted as long as it can be used for culture of animal cells, and examples thereof include Neurobasal medium, Neural Progenitor Basal medium, NS-A medium, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, DMEM/F12 medium, Ham's medium, RPMI 1640 medium and Fischer's medium, and mixed media thereof. The basal medium is preferably a mixture of Neurobasal medium and DMEM/F12. Examples of the additive(s) include serum, retinoic acid, Wnt, BMP, bFGF, EGF, HGF, Sonic hedgehog (Shh), brain-derived neurotrophic factor (BDNF), glial cell line-derived neurotrophic factor (GDNF), neurotrophin-3 (NT-3), insulin-like growth factor (IGF1), amino acids, vitamins, interleukins, insulin, transferrin, heparin, heparan sulfate, collagen, fibronectin, progesterone, selenite, B27-supplement, N2-supplement, ITS-supplement and antibiotics. Preferred additives are retinoic acid, Shh, BDNF, GDNF, NT-3, B27-supplement and N2-supplement. Combination of the additives may be changed in a stepwise manner, and the culture is preferably first carried out in a medium supplemented with retinoic acid, Shh, B27-supplement and N2-supplement, and then in a medium supplemented with BDNF, GDNF, NT-3, B27-supplement and N2-supplement.

The concentration of the neural stem cells may be set appropriately to allow efficient formation of nerve cells. The concentration of the neural stem cells at the beginning of the culture is not restricted, and, for example, about $1 \times 10^3$ to about $1 \times 10^6$ cells/ml, preferably about $1 \times 10^4$ to about $5 \times 10^5$ cells/ml.

Other culture conditions such as the culture temperature and the $CO_2$ concentration may be set appropriately. The culture temperature is not restricted, and, for example, about 30 to 40° C., preferably about 37° C. The $CO_2$ concentration is, for example, about 1 to 10%, preferably about 5%. The $O_2$ concentration is 1 to 20%.

The culturing period after separation of a neurosphere and adhesion thereof on a culture dish is not restricted, and preferably not less than 5 days, more preferably 14, 21, 22 or 28 days.

The nerve cells can be characterized by their ability to express BF1, βIII tubulin, TuJ1, NeuN, 160 kDa neurofilament protein, MAP2ab, glutamate, synaptophysin, glutamic acid decarboxylase (GAD), tyrosine hydroxylase, GABA, serotonin, GFAβ, Foxg1, Cux1, Satb2, Tbr1, Ctip2 and Synapsin, but the indices for characterization of the nerve cells is not restricted thereto.

IV. Method for Measuring Amount of Causative Protein

In the present invention, in cases where the causative protein is an intracellular protein, the amount of the protein may be measured using a lysate of nerve cells derived from iPS cells. On the other hand, in cases where the causative protein is a secretory protein, the amount of the protein contained in the culture liquid may be measured. Here, for the measurement, a per se known method may be used. Examples of the measurement method in cases where the causative protein is Aβ are described below.

In the present invention, "Aβ" means amyloid β-peptide, which is a protein fragment produced by cleavage of amyloid precursor protein (APP) by β- and γ-secretase, and the amyloid β-peptide is preferably constituted by 40 amino acid residues (Aβ40) or 42 amino acid residues (Aβ42). Therefore, the amount of Aβ used in the present invention may be the concentration of Aβ40 or Aβ42 secreted into the culture liquid, and may preferably be the ratio of abundance of Aβ42 with respect to Aβ40 (Aβ42/Aβ40), full-length amyloid precursor proteins (FL-APP), housekeeping gene (ex. β-actin, HPRT, GAPDH, and HSP90) or nerve cell marker (ex. βIII tubulin, TuJ1, NeuN, 160 kDa neurofilament protein, MAP2ab, glutamate, synaptophysin, GAD, tyrosine hydroxylase, GABA, serotonin, GFAβ, Foxg1, Cux1, Satb2, Tbr1, Ctip2 and Synapsin).

The diagnosis or prediction of the age of onset of Alzheimer's disease of the present invention may be carried out by measuring the concentration of Aβ in the culture liquid of nerve cells derived from iPS cells obtained as described above. Here, the measurement of the concentration of Aβ can be carried out by using a per se known method. Examples of the method include ELISA, Western blotting, immunoprecipitation, slot or dot blot assay, immunohistostaining, radioimmunoassay (RIA), fluoroimmunoassay, and immunoassay using the avidin-biotin or streptavidin-biotin system.

The amount of Aβ obtained as described above can be used as intermediate data for diagnosis of Alzheimer's disease by a physician or the like.

V. Method of Measurement of Activity or Expression Level of Enzyme Involved in Degradation of Causative Protein In the present invention, measurement of the activity of the enzyme involved in degradation of the causative protein can be carried out by measuring the amount of degradation of the causative protein or a fragment thereof as a substrate of the enzyme. In cases where the enzyme involved in degradation of the causative protein is an intracellular protein, a lysate of nerve cells derived from iPS cells may be brought into contact with the substrate, followed by measuring the amount of degradation of the substrate. On the other hand, in cases where the enzyme involved in degradation of the causative protein is a secretory protein, the culture liquid may be brought into contact with the substrate, followed by measuring the amount of degradation of the substrate. Here, the measurement of degradation of the substrate may be carried out by using a per se known method. Since the activity of the enzyme involved in degradation of the causative protein is considered to be proportional to the expression level of the gene encoding the enzyme or the amount of protein translated from the gene (these are referred to as the expression level of the enzyme), the expression level of the enzyme may also be used as an index. The expression level of the gene encoding the enzyme can be measured by RT-PCR, Northern blotting or the like, and the amount of protein translated from the gene can be measured by ELISA, Western blotting or the like.

The enzyme activity may preferably be represented as the amount of the substrate degraded during a certain period of time per unit number of cells. Here, the total protein mass in the cell lysate may be used as an alternative to the number of cells. Examples of the method for measuring the activity in cases where the enzyme involved in degradation of the causative protein is neprilysin are described below.

In the present invention, neprilysin (EC 3.4.24.11) as an example of the enzyme involved in degradation of the causative protein is a membrane-bound neutral endopeptidase that exists in various animal tissues and whose active site is oriented toward the outside of the cells. In rat brain, neprilysin was discovered as an enkephalin-degrading peptidase, and it is also called enkephalinase. Existence of plural types of peptides that may be substrates of neprilysin has been revealed by in vitro experiments, and examples of the peptides include enkephalin, substance P, atrial natriuretic peptide (ANP), gastrin releasing peptide (GRP) and endothelin.

The activity of neprilysin can be measured by, for example, the method described in JP 2002-34596 A or JP 2004-151079 A. The activity of neprilysin is preferably represented by the amount of an artificial substrate cleaved by a specific amount of the protein in a nerve cell extract in a given period of time. More particularly, a substrate of neprilysin is allowed to react with the nerve cells, the nerve cells that was fixed, a cell lysate of the nerve cells, neprilysin purified from the nerve cells, or the like, followed by calculation based on the amount of degradation of the substrate.

Here, examples of the substrate of neprilysin include, in addition to the substrates mentioned above, synthetic substrates such as benzyloxycarbonyl-alanyl-alanyl-leucyl-paranitroanilide, benzyloxycarbonyl-alanyl-alanyl-phenylalanyl-paranitroanilide, benzyloxycarbonyl-glycyl-glycyl-leucyl-paranitroanilide, benzyloxycarbonyl-glycyl-glycyl-phenylalanyl-paranitroanilide, glutaryl-alanyl-alanyl-phenylalanyl-4-methoxy-2-naphthylamide, glutaryl-alanyl-alanyl-phenylalanyl-2-naphthylamide, and succinyl-alanyl-alanyl-phenylalanine-4-methylcoumarin-7-amide, but the substrate is not limited thereto.

The reaction conditions may be selected appropriately by those skilled in the art depending on the substrate used. For example, although the concentration of the substrate varies depending on the type of the substrate to be used, the reaction may be carried out with a substrate at a concentration of 0.1 to 1000 µg/ml. The concentration of the substrate is preferably 1 to 100 µg/ml, more preferably 3 to 30 µg/ml in the reaction system. The reaction temperature is preferably 20° C. to 45° C., more preferably 20° C. to 40° C. The reaction time varies depending on the conditions of the reaction system such as the type of the substrate to be used and the concentration thereof. For example, it may be appropriately selected within the range of 5 minutes to 24 hours, and, in view of rapidity, the reaction system is preferably designed such that the measurement can be carried out in a short period of time such as 5 minutes to 60 minutes. The reaction is preferably carried out at a neutral pH, that is, pH 6 to 9, more preferably pH 7 to 8.

The amount of degradation of the substrate may be determined by measuring the concentration of a compound obtained after the degradation. The method of measurement is not restricted, and, in cases where the compound obtained by the degradation emits fluorescence or in cases where the compound obtained by the degradation reacts with a reagent to emit fluorescence, the amount of degradation can be measured by measuring the fluorescence intensity. As another embodiment, the amount of degradation of the substrate may be analyzed by thin layer chromatography, HPLC or the like. In such a case, the amount of degradation may be corrected by a measured value obtained after addition of an inhibitor (e.g., thiorphan). The activity of neprilysin may be represented by the amount of degradation of a substrate per unit number of cells.

The activity of neprilysin obtained as mentioned above can be used as intermediate data for diagnosis of Alzheimer's disease by a physician or the like.

IV. Method of Diagnosis of Onset and Risk of Development of Protein Misfolding Disease By comparing the amount of a causative protein in nerve cells derived from iPS cells obtained from a test subject with the amount of the same protein in control cells, or by comparing the activity or the expression level of an enzyme involved in degradation of a causative protein in nerve cells derived from iPS cells obtained from a test subject with the activity or the expression level of the same enzyme in control cells, onset of and/or the risk of development of a protein misfolding disease can be judged.

Examples of the control cells include nerve cells produced by differentiation induction of iPS cells obtained from somatic cells derived from a control subject (e.g. normal subject) who has not developed a protein misfolding disease, and nerve cells produced by differentiation induction of iPS cells obtained from somatic cells derived from a control subject (patient) who has developed a protein misfolding disease.

In cases where the control cells are nerve cells produced by differentiation induction of iPS cells obtained from somatic cells derived from a control subject who has not developed a protein misfolding disease, a test subject can be judged as having developed the protein misfolding disease and/or having a risk of developing it when the amount of a causative protein in the cells derived from the test subject is higher than the amount of the causative protein in the control cells, or when the activity or the expression level of an enzyme involved in degradation of a causative protein in the cells derived from the test subject is lower than the activity or the expression level of the enzyme in the control cells.

On the other hand, in cases where the control cells are nerve cells produced by differentiation induction of iPS cells obtained from somatic cells derived from a control subject who has developed a protein misfolding disease, a test subject can be judged as having developed the protein misfolding disease or having a risk of developing it when the amount of a causative protein in the cells derived from the test subject is equivalent to or higher than the amount of the causative protein in the control cells, or when the activity or the expression level of an enzyme involved in degradation of a causative protein in the cells derived from the test subject is equivalent to or lower than the activity or the expression level of the enzyme in the control cells.

In the present invention, the protein misfolding disease, of which onset and/or the risk of development are to be diagnosed, is Alzheimer's disease as an example, and the diagnosis may be carried out for either familial or sporadic Alzheimer's disease. Familial Alzheimer's disease is exemplified as the Alzheimer's disease. In a more preferred embodiment, the Alzheimer's disease is early-onset Alzheimer's disease.

In the present invention, in cases where the protein misfolding disease is Alzheimer's disease, the amount of Aβ as a causative protein is preferably measured as the amount thereof in the culture supernatant of nerve cells produced by differentiation induction of iPS cells established from somatic cells of the test subject. Similarly, the activity of neprilysin as an enzyme involved in degradation of the causative protein is preferably measured using a cell lysate or the like.

As another embodiment, the amount of a causative protein, or the activity or the expression level of an enzyme involved in degradation of a causative protein in control cells may be preliminarily measured to prepare Table 1 or Table 2, and the judgment may be made using a reference value determined such that both the sensitivity and the specificity shown in Table 1 or Table 2 are not less than 0.9, preferably not less than 0.95, more preferably not less than 0.99. Especially preferably, both the sensitivity and the specificity are 1. Here, the fact that both the sensitivity and the specificity are 1 means that the reference value is ideal, producing neither false-positive nor false-negative result at all. In the judgment, in cases where the amount of a causative protein such as Aβ in the culture supernatant of the cells derived from a test subject is higher than the reference value, the test subject can be judged as having developed a protein misfolding disease or having a risk of development thereof. Similarly, in cases where the activity or the expression level of an enzyme involved in degradation of a causative protein in the cells derived from a test subject is lower than the reference value, the test subject can be judged as having developed a protein misfolding disease or having a risk of development thereof.

TABLE 1

Table for measurement of the amount of a causative protein

| | Number of cases wherein onset of protein misfolding disease has not been confirmed | Number of cases wherein onset of protein misfolding disease has been confirmed |
|---|---|---|
| Number of cases wherein amount of causative protein is higher than reference value | A | C |
| Number of cases wherein amount of causative protein is not more than reference value | B | D |
| | Specificity = B/(A + B) | Sensitivity = C/(C + D) |

TABLE 2

Table for measurement of the activity or the expression level of the gene involved in a causative protein

| | Number of cases wherein onset of protein misfolding disease has not been confirmed | Number of cases wherein onset of protein misfolding disease has been confirmed |
|---|---|---|
| Number of cases wherein activity or expression level of gene involved in degradation of a causative protein is lower than reference value | A | C |
| Number of cases wherein activity or expression level of gene involved in degradation of a causative protein is not less than reference value | B | D |
| | Specificity = B/(A + B) | Sensitivity = C/(C + D) |

The diagnosis of a protein misfolding disease may be carried out in combination with another diagnostic method such as a method based on findings from the PET or MRI exam of the patient, or a neuropsychological test for the cognitive function including WMS-R logical memory score, MMSE or ADAS-Jcog.

V. Method for Prediction of Age of Onset of Protein Misfolding Disease

By comparing the amount of a causative protein in nerve cells produced by differentiation induction of iPS cells established from somatic cells of a test subject with the amount of the protein in control cells, or by comparing the activity or the expression level of an enzyme involved in degradation of a causative protein in such nerve cells derived from a test subject with the activity or the expression level of the enzyme in control cells, and when the compared values are equivalent between the nerve cells derived from the test subject and the control cells, it is indicated that the test subject develops the protein misfolding disease at the same age as the age when the control subject from whom the control cells were derived has developed the disease.

In the present invention, the protein misfolding disease for which the age of onset is to be predicted is Alzheimer's disease as an example, and the prediction may be carried out for either familial or sporadic Alzheimer's disease. The familial Alzheimer's disease is exemplified as the Alzheimer's disease. In a more preferred embodiment, the Alzheimer's disease is early-onset Alzheimer's disease (juvenile Alzheimer's disease).

In the present invention, in cases where the protein misfolding disease is Alzheimer's disease, the amount of Aβ as a causative protein is preferably measured as the amount thereof in the culture supernatant of nerve cells produced by differentiation induction of iPS cells established from somatic cells of the test subject. Similarly, the activity of neprilysin as an enzyme involved in degradation of the causative protein is preferably measured using a cell lysate or the like.

In the judgment of the age of onset of a protein misfolding disease, the control cells are preferably nerve cells produced by differentiation induction of iPS cells established from somatic cells of a control subject (patient) whose age of onset of the protein misfolding disease is known.

The term "equivalent" includes a case where the value is strictly identical as well as a case where an error preferably within the range of ±5% exists with respect to the measured value. Similarly, "the same age" may include an error within the range of ±5% with respect to the age or age within decade.

As another embodiment, it is preferred to judge the age of onset by preliminarily measuring the amount of a causative protein or the activity or the expression level of an enzyme involved in degradation of a causative protein in control cells to determine the reference range of the measured value for each age unit of every 10 years old, preferably every 5 years old, more preferably every 1 year old, followed by comparing the reference range with the measured value in a test subject.

VI. Kit for Diagnosis of, or for Prediction of Age of Onset of, Protein Misfolding Disease The kit of the present invention for diagnosis of, or for prediction of the age of onset of, a protein misfolding disease comprises: (a) a reprogramming substance(s) for production of iPS cells, (b) a reagent(s) for differentiation induction into nerve cells, and (c) a reagent for measurement of the amount of a causative protein or a reagent for measurement of the activity or the expression level of an enzyme involved in degradation of a causative protein.

As the reprogramming substance(s) for production of iPS cells, the reprogramming substances exemplified in the above-mentioned production of iPS cells may be used. To enhance the efficiency of induction of iPS cells upon the nuclear reprogramming, another factor may also be included in the reprogramming substances. The reprogramming substances preferably contain at least one factor selected from the group consisting of the OCT family, MYC family, KLF family and SOX family.

As the reagent(s) for differentiation induction into nerve cells, the reagents described in the above-mentioned methods for differentiation induction into neural stem cells and for differentiation induction into nerve cells may be used. The reagents are preferably those described in the method for differentiation induction into nerve cells, and more preferably contain at least one factor selected from the group consisting of BDNF, GDNF and neurotensin-3.

The reagent for measurement of the amount of a causative protein is preferably a reagent for measurement of the amount of Aβ, and, as the reagent, the reagents described in the above-mentioned method for measuring the amount of Aβ may be used. The reagent is preferably an antibody specific to Aβ40 and/or Aβ42 used for the ELISA method.

The reagent for measurement of the activity of an enzyme involved in degradation of a causative protein is preferably a reagent for measuring the activity of a protease, and more preferably contains a causative protein or a fragment thereof as a substrate of the protease. For example, the reagent for measurement of activity of an enzyme involved in degradation of a causative protein is a reagent for measuring activity of neprilysin, and the reagents described in the above-mentioned method for measuring the activity of neprilysin may be used. In this case, the reagent preferably contains a substrate of neprilysin, more preferably succinyl-alanyl-alanyl-phenylalanine-4-methylcoumarin-7-amide. The reagent for measuring activity of neprilysin may further contain an inhibitor or activator of neprilysin for measurement of a control value, and the inhibitor is preferably thiorphan.

The reagent for measuring the expression level of an enzyme involved in degradation of a causative protein preferably contains an antibody against the enzyme, PCR primers or a hybridization probe specific to the gene of the enzyme, or the like.

The kit of the present invention for diagnosis of, or prediction of the age of onset of, a protein misfolding disease may comprise means of screening such as a document or instruction wherein a procedure of the screening is described; a program(s) for execution of a procedure of the screening on a computer; a computer-readable storage medium wherein a list of the program(s) and the program(s) are recorded (e.g., flexible disk, optical disk, CD-ROM, CD-R, CD-RW or the like); and/or a device or system (e.g., computer) for carrying out the screening.

The present invention will now be described more concretely by way of Examples, but, needless to say, the present invention is not restricted thereto.

EXAMPLES

Example 1 iPS Cells

253G4 described in Nakagawa M, et al., Nat Biotechnol. 2008 January; 26(1):101-6. was used as the iPS cell. Briefly, the iPS cells were established by introducing Oct3/4, Sox2 and Klf4 to fibroblasts derived from a Caucasian female of 36 years old.

Formation of Neurosphere

The formation of a neurosphere was carried out by the method described in Wada T, et al, PLoS ONE 4(8), e6722, 2009 with a slight modification. More particularly, the iPS cells were divided into small clusters and cultured using N2B27 medium (Gibco) prepared by mixing DMEM/F12 and Neurobasal medium A together at a volume ratio of 1:1 and adding 1% N2, 2% B27 and 200 μM glutamine thereto, in a dish coated with poly-L-lysine/laminin (PLL/LM) (Sigma-Aldrich). Further, to this medium, Noggin (R&D systems) was added at 100 ng/ml. The medium was replaced with a medium containing 100 ng/ml Noggin every 3 days, and, after 10 days of culture, the cells were subcultured to a PLL/LM-coated dish. Thereafter, the medium was replaced with a medium containing 100 ng/ml Noggin every other day, followed by plating the cells in a 2-hydroxyethylmetacrylate (HEMA)-coated dish at a concentration of 1,000,000 cells/ml on Day 7. At this time, N2B27 medium supplemented with 20 ng/ml EGF (R&D systems), 20 ng/ml bFGF and 50 ng/ml heparin (Sigma-Aldrich) was used. All these cultures were carried out by incubation at 37° C. under a humidified atmosphere of 5% $CO_2$. The subculturing was carried out every 30 days with pipetting, and the medium was replaced every 7 days.

Differentiation Induction into Nerve Cells

A secondary neurosphere, which was prepared by subculturing the above-mentioned neurosphere to allow formation of a neurosphere again, was separated using Accutase (Innovative Cell Technologies), and plated at a concentration of 15,000 cells/ml on a PLL/LM/fibronectin-coated dish containing N2B27 medium supplemented with 1 μM retinoic acid (Sigma-Aldrich) and 100 ng/ml sonic hedgehog (R&D systems). The medium was replaced every other day. Seven days after the plating, the medium was replaced with N2B27 medium supplemented with 10 ng/ml brain-derived neurotrophic factor (BDNF) (R&D systems), 10 ng/ml glial cell line-derived neurotrophic factor (GDNF) (R&D systems) and 10 ng/ml neurotensin-3 (NT-3) (R&D systems). By this method, TuJ1-positive cells were obtained, and differentiation induction into nerve cells was confirmed.

Analysis of Aβ Concentration in Nerve Cells

After separation of a secondary neurosphere as described above, the secondary neurosphere was allowed to adhere to a dish, followed by culturing it for 4 days or 22 days, after which the culture supernatant of the nerve cells was collected. The culture supernatant was centrifuged at 4° C. at 3,000 rpm for 5 minutes to remove the precipitate before use. By ELISA using a combination of a capture antibody that recognizes an internal sequence (17-24) of the Aβ peptide and a detection antibody that recognizes the carboxyl terminus (Wako Pure Chemical Industries, Ltd.), the contents of Aβ(1-40) and Aβ(1-42) were measured by duplicate assay for each of 3 lots. The concentration of Aβ was calculated based on a calibration curve prepared using synthetic peptides of Aβ(1-40) and Aβ(1-42). The measurement results represented as the mean±SE among the lots of nerve cells are shown in panels A to C in FIG. 1. The obtained values were as follows.

4-day culture
Aβ(1-40): Mean 28.5 pM (28.4 pM, 38.1 pM, 19.1 pM)
Aβ(1-42): Below detection limit
22-day culture
Aβ(1-40): Mean 67.5 pM (95.7 pM, 52.5 pM, 54.1 pM)
Aβ(1-42): Mean 8.4 pM (11.0 pM, 5.6 pM, 8.6 pM)
Aβ(1-42)/Aβ(1-40): 0.124

Analysis of Measurement of Neprilysin Activity in Nerve Cells

After separation of a secondary neurosphere as described above, the secondary neurosphere was allowed to adhere to a dish, followed by culturing it for 4 days or 22 days, after which the cells were collected. The collected cells were lysed using 50 μL of 1% triton/50 mM Tris-HCl, 150 mM NaCl, Complete (EDTA free), Z-Leu-Leu-Leu-H (aldehyde)

[MG132], pepstatin A, pH 7.4. The cell lysate was mixed with an artificial substrate (Succinyl-Ala-Ala-Phe-MCA, Bachem AG.), and was incubated for 1 h at 37° C. To the reaction mixture was then added leucine aminopeptidase (L-5006; Sigma, St Louis, Mo., USA) and phosphoramidon (Peptide Institute, Osaka, Japan), followed by further incubation for 30 min at 37° C. to remove a phenylalanine residue from Phe-AMC formed by neutral endopeptidase-catalyzed digestion. The fluorescence intensity of the liberated AMC (7-amino-4-methylcoumarin) was measured. The amount of the degradation product was determined based on a calibration curve of the fluorescence intensity-concentration prepared by using a dilution series of a standard product AMC. The difference between the obtained value and a value determined by measurement in the same manner after addition of thiorphan, a specific inhibitor of neprilysin, was calculated as the activity of neprilysin. The protein concentration in the cell lysate was determined using the BCA kit. The enzyme activity was represented as the amount of the artificial substrate cleaved by a specific amount of the protein (nmol/mg protein/min) in the nerve cell extract. It has been revealed that the enzyme activity calculated by this method value correlates with the abundance of the neprilysin protein in most cases. The measurement was carried out by duplicate assay for each of 3 lots, and the results are shown in panel D in FIG. 1. The value was below the detection limit on Day 4, but the mean on Day 22 was 1.831 (nmol/mg protein/min). Thus, since the number of differentiated nerve cells increased as the days of culture increased, higher values were obtained on Day 22 than on Day 4.

The amount of secretion of Aβ from nerve cells produced by differentiation induction of iPS cells and the neprilysin activity can be measured as described above. Further, since it can be easily understood that the measured values may change when the genetic background is different, it is suggested that the onset of Alzheimer's disease can be correlated with the measured values of the respective markers in nerve cells produced by differentiation induction of iPS cells.

Example 2

Method of Differentiation into Nerve Cells

Figure 2:
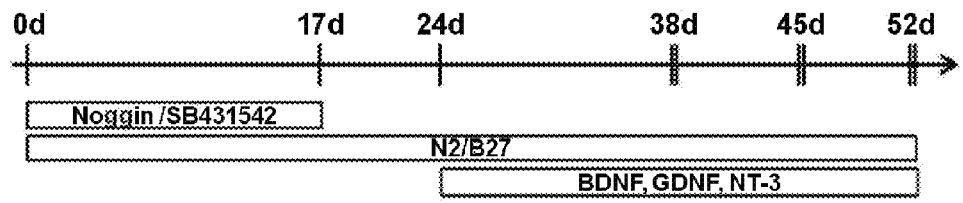
FIG. 2 shows the protocol of differentiation induction to nerve cells. N2B27 means the medium containing N2 and B27 supplement.
Figure 3:
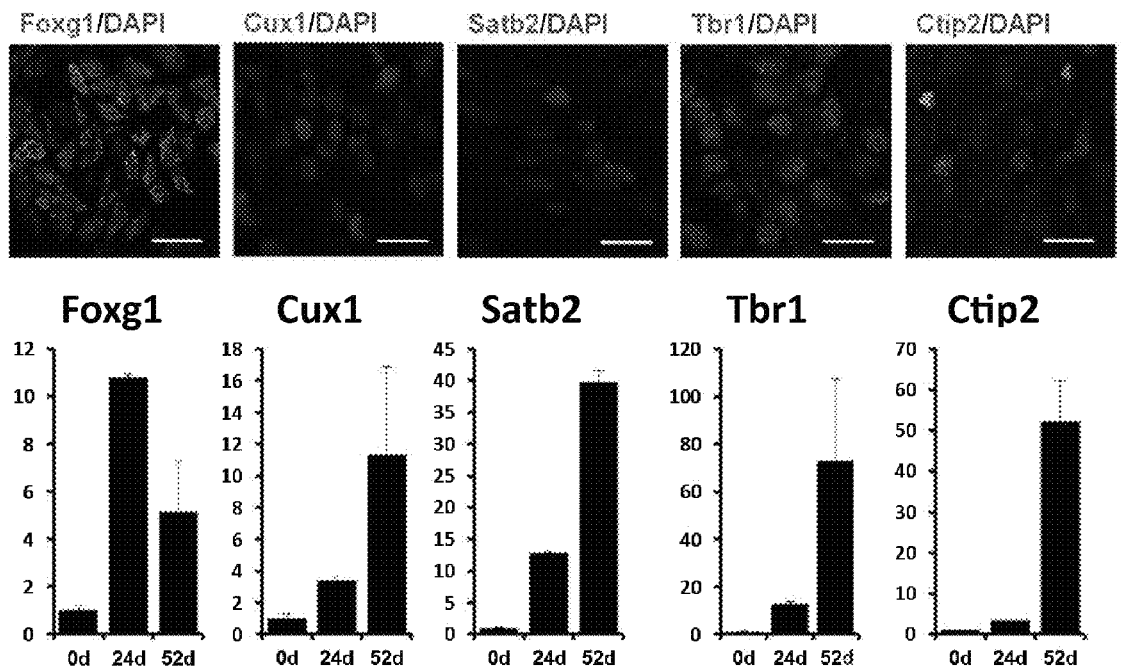
FIG. 3 shows the image of immunostaining for Foxg1 (green), Cux1 (red), Satb2 (red), Tbr1 (green) and Ctip2 (green) at 52 days after differentiation induction (upper; photograph), and the results of measurement of relative expression amount of Foxg1, Cux1, Satb2, Tbr1 and Ctip2 mRNA (lower) in nerve cells derived from iPS cells (253G4). The value at 38 days is used as standard. The mean±SE among three times is shown.
Figure 6:
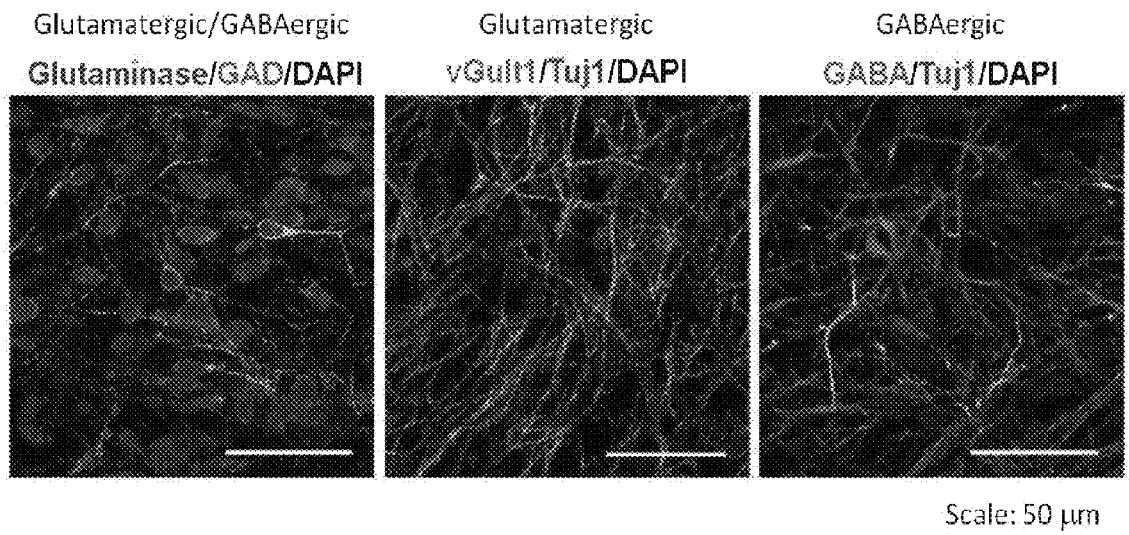
FIG. 6 shows the image of immunostaining for Glutaminase, GAD, vGult1, Tuj1, GABA at 52 days from differentiation induction (photograph). Glutaminase and GAD are shows by red and green respectively (left). vGult1 and Tuj1 are shows by green and red respectively (middle). GABA and Tuj1 are shows by green and red respectively (right). Scale bar in each figure means 50 μm.

Human iPS cell line 253G4 were cultured on mitomycin C-treated mouse embryonic fibroblasts in primate ES medium (ReproCELL) supplemented with bFGF (Wako). To obtain neurons derived from the iPS cell line, the reported method was partially modified (Wada, T. et al 2009, Chambers, S. M. et al 2009). Briefly, small clumps of iPS cell colonies (40-100 µm in diameter) were selected with Cell Strainer (BD Falcon) and plated on poly-L-lysine (Sigma)/Laminin (BD Falcon) (PLL/LM) coated dishes in N2B27 medium [DMEM/F12, Neurobasal, N2 supplement, B27 supplement, L-Gln], supplemented 100 ng/ml human recombinant Noggin (R&D systems) and 1 µM of SB431542 (Sigma) for 10 days. Then the colonies were dissociated into small clumps by 200 U/ml Collagenase with CaCl2 and plated into PLL/ECL (Millipore) coated dishes. After 7 days culturing, the cells were dissociated by Accutase (Innovative Cell Technologies) and cultured on PLL/ECL coated dishes for 7 days (24 d). Finally, the cells dissociated by Accutase and selected with 40 µm cell strainer (BD Falcon) were counted and cultured on PLL/LM/Fibronectin (Millipore) coated dishes in N2B27 medium supplemented with 10 ng/ml BDNF, GDNF, and NT-3 (R&D systems) for 14 days (38 d), 21 days (45 d) or 27 days (52 d). The protocol of the induction of differentiation was shown in FIG. 2.

Evaluation of Nerve Cells Derived from iPS Cells

The nerve cells obtained with above differentiated method were evaluated by immunocytochemistry and quantitative real-time PCR (q-PCR). These methods are well known in the art. Primer pairs used in q-PCR are listed in the Table 3. Expression of Foxg1, Cux1, Satb2, Tbr1, Ctip2, Tuj1, GFAβ, Synapsin I, Glutaminase, GAD, vGult1, GABA and Tau were shown in FIGS. 3, 4, 5 and 6. From these result, the cells differentiated from iPS cells (52 d) were confirmed to be neurons including Glutamatergic and GABAergic cells.

TABLE 3

Table for list of primer pairs

| | Forward | Reverse |
|---|---|---|
| FoxG1 | tactaccgcgagaacaagca (SEQ ID NO: 1) | tcacgaagcacttgttgagg (SEQ ID NO: 2) |
| Cux1 | cagatgtccaccacctcaaa (SEQ ID NO: 3) | ggtcaaataattctgttcgagtttt (SEQ ID NO: 4) |
| Satb2 | cctcctccgactgaagacag (SEQ ID NO: 5) | tggtctgggtacaggcctac (SEQ ID NO: 6) |
| Tbr1 | gcacaagcagcaagatcaaa (SEQ ID NO: 7) | caaccagcaaatgcttctca (SEQ ID NO: 8) |
| Ctip2 | atcctcagcccctttgttt (SEQ ID NO: 9) | gccgttgttcctgaattgtt (SEQ ID NO: 10) |
| Tuj1 | aacgaggcctcttctcacaa (SEQ ID NO: 11) | ggcctgaagagatgtccaaa (SEQ ID NO: 12) |
| GFAP | ggttgagagggacaatctgg (SEQ ID NO: 13) | aggttgttctcggcttcca (SEQ ID NO: 14) |
| Synapsin I | gacggaagggatcacatcat (SEQ ID NO: 15) | ctggtggtcaccaatgagc (SEQ ID NO: 16) |

Figure 7:
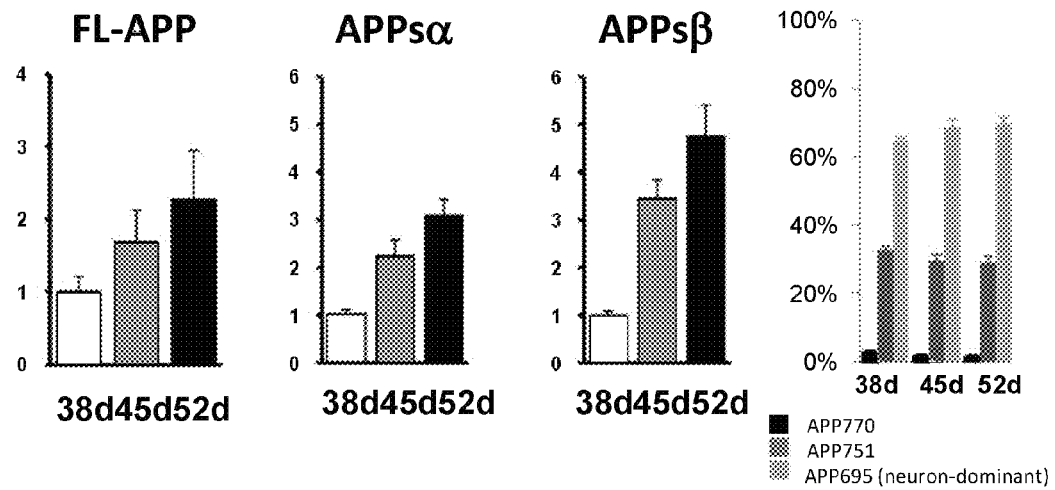
FIG. 7 shows the results of measurement of relative expression amount of full-length APP (FL-APP), a soluble form of APP α (APPsα) and a soluble form of APP β (APPsβ), and the results of mRNA expression ratio of APP splicing variant (APP770, APP751 and APP695) in nerve cells derived from iPS cells (253G4) at each term. The value at 38 days is used as standard.
Figure 8:
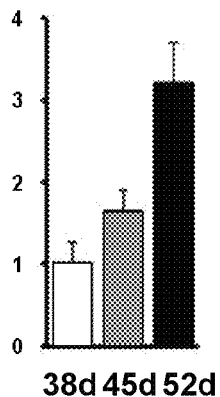
FIG. 8 shows the results of measurement of relative expression amount of BACE1 protein in nerve cells derived from iPS cells (253G4) at each term. The value at 38 days is used as standard.
Figure 9:
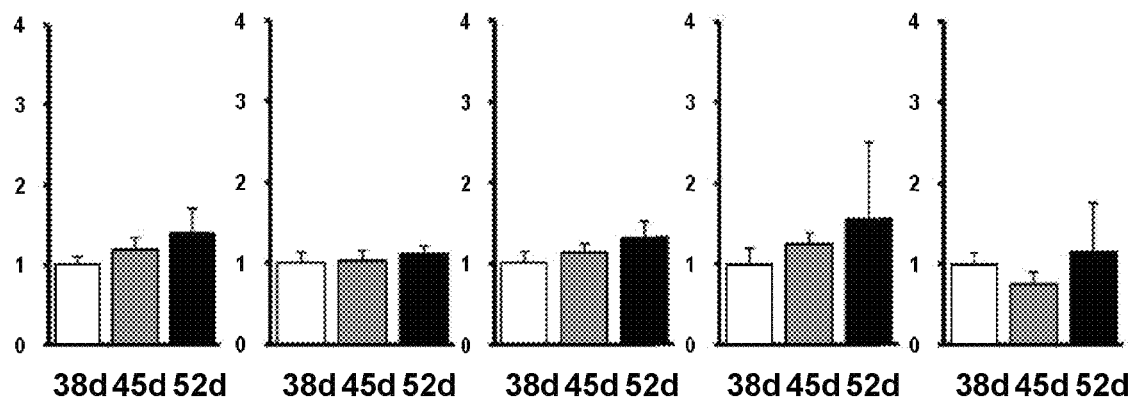
FIG. 9 shows the results of measurement of relative expression amount of Presenilin 1, Nicastrin and Pen2 protein, and relative expression amount of Aph-1A and Aph-1B mRNA in nerve cells derived from iPS cells (253G4) at each term. The value at 38 days is used as standard.
Figure 10:
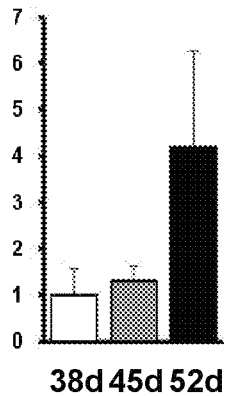
FIG. 10 shows the results of measurement of relative expression amount of Neprilysin mRNA in nerve cells derived from iPS cells (253G4) at each term. The value at 38 days is used as standard.

The level of FL-APP (full length amyloid β protein precursor), APPs alpha (APPsα) and APPs beta (APPsβ) in the differentiated cell at 38 d, 45 d and 52 d were quantified by western blot analysis using 6E10 or 22C11 antibody (FIG. 7). Furthermore, expression ratio of 3 types of APP splicing variant (APP770, APP751 and APP695) were estimated from a difference of molecular size of each variant on the same Western blot membrane. The neuron-dominant type (APP695) was major splicing variant in the neuron derived iPS cells. The expression of beta-secretase (BACE1) and gamma-secretase component genes (Presenilin 1, Nicastrin and Pen-2) were measured by western blotting, and other gamma-secretase component genes (Aph-1A and Aph-1B) and neprilysin were measured by q-PCR with primer pairs listed in Table 4. These results showed that gamma-secretase component genes were matured at 38 day from differentiation, but beta-secretase and neprilysin required more terms of differentiation.

TABLE 4

Table for list of primer pairs

| | Forward | Reverse |
|---|---|---|
| Aph-1A | gcttcgcgttatcatcctg (SEQ ID NO: 17) | ccaagatgaaccagaccaca (SEQ ID NO: 18) |
| Aph-1B | aagtgggcatcctccttat (SEQ ID NO: 19) | tgacgccaggtttattccata (SEQ ID NO: 20) |
| Neprilysin | atgctgtgggaggctttat (SEQ ID NO: 21) | ctcggatctgtgcaatcaaa (SEQ ID NO: 22) |

Analysis of Aβ Concentration in Nerve Cells

Figure 11:
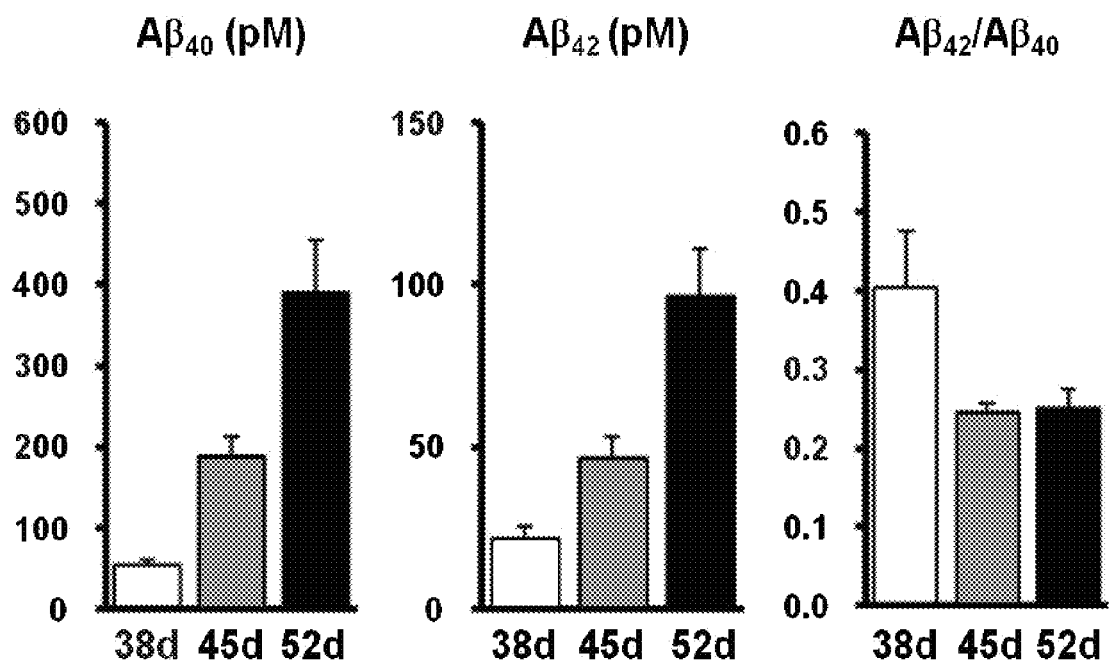
FIG. 11 shows the results of measurement of the contents of Aβ40 (left) and Aβ42 (middle) in the culture media of nerve cells derived from iPS cells (253G4), and the Aβ42/Aβ40 ratio (right).
Figure 12:
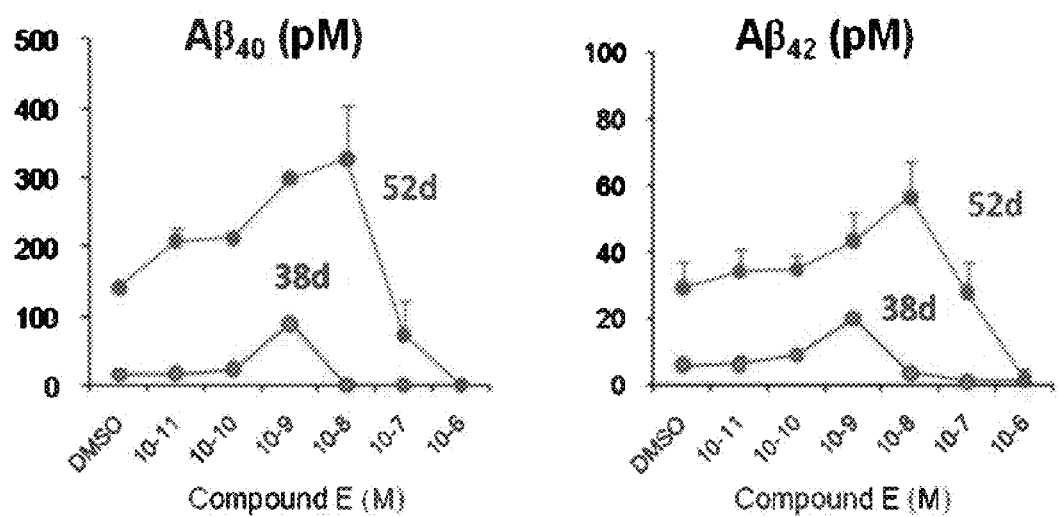
FIG. 12 shows the results of measurement of the contents of Aβ40 (left) and Aβ42 (right) in the culture media of nerve cells derived from iPS cells (253G4) at 38 and 52 days. The abscissa indicates concentration of γ-secretase inhibitor, Compound E. DMSO means absence of Compound E.

The contents of Aβ(1-40) and Aβ(1-42) in the nerve cells derived from iPS cells were measured with the ELISA method described in Example 1. The concentration of Aβ40 and Aβ42 and ratio (Aβ42/Aβ40) were shown in FIG. 11. γ-Secretase inhibitor (compound E) was tested for confirmation whether secretion of Aβs was produced from APP C-terminal fragment by γ-secretase-dependent cleavage (FIG. 12).

Consequently, it was confirmed that γ-secretase also played an important role in secretion of Aβs in the case of neurons derived from iPS cells.

Example 3 iPS Cells

Alzheimer's disease (AD)-iPS cell line was established by using the method described in Takahashi K, et al, Cell. 131: 861-72, 2007. Briefly, the iPS cells were established by introducing Oct3/4, Sox2, Klf4 and c-Myc to fibroblasts derived from Sporadic AD patient who has the ApoE 3/4 isoform and has an onset of the disease in 50's.

Method of Differentiation into Neurons

Figure 13:
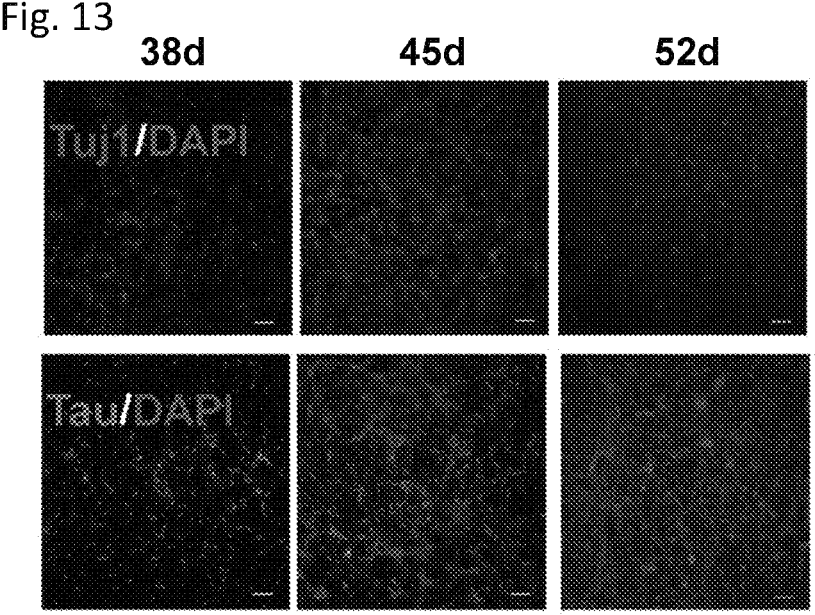
FIG. 13 shows the image of immunostaining for Tuj1 (red) and Tau (green) at 38, 45, and 52 days after differentiation induction (photograph).
Figure 14:
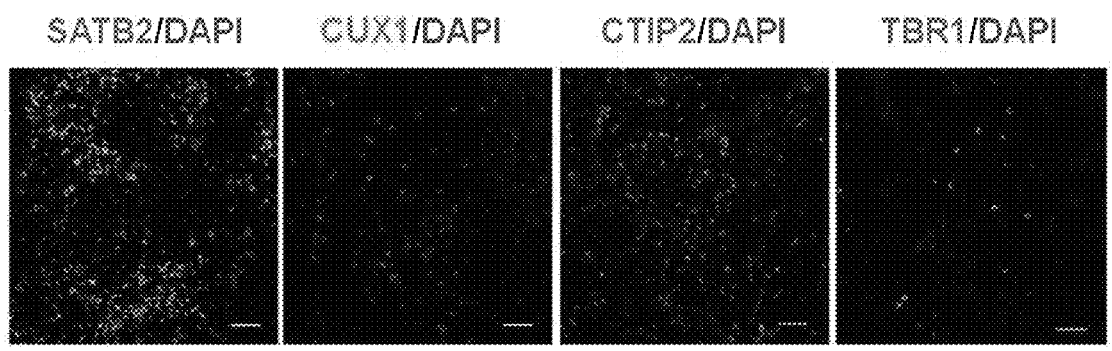
FIG. 14 shows the image of immunostaining for SATB2 (green), CUX1 (red), CTIP2 (green) and TBR1 (green) at 52 days from differentiation induction (photograph).
Figure 15:
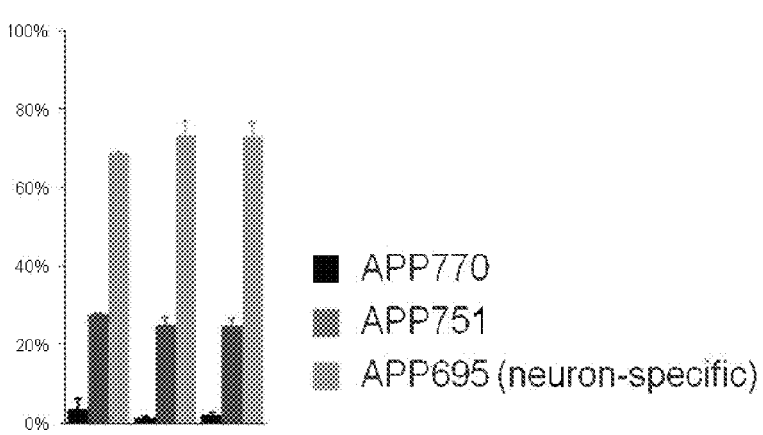
FIG. 15 shows the results of mRNA expression ratio of APP splicing variant (APP770, APP751 and APP695) in nerve cells derived from Alzheimer's disease (AD)-iPS cells at each term.

To obtain neurons derived from AD-iPS cell line, the method described in Example 2 was used. The neurons were evaluated with expression of Tuj1, Tau, SATB2, CUX1, CTIP2 and TBR1 (FIGS. 13 and 14). It was observed that expression of the neuron related genes in AD-iPS cell line was indistinct from that of normal iPS cell line described in Example 2.

Analysis of Aβ Concentration in Nerve Cells

Figure 16:
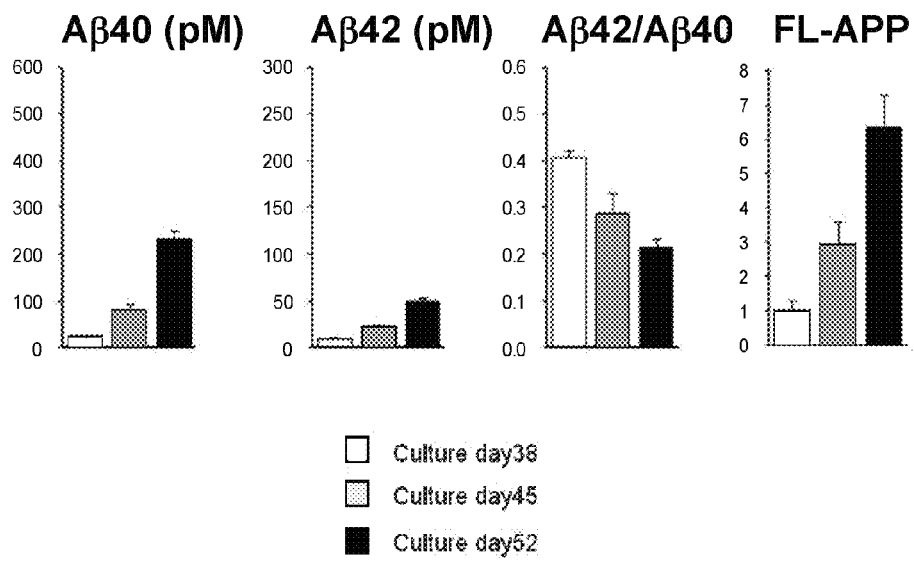
FIG. 16 shows the results of measurement of the contents of Aβ40 and Aβ42 in the culture supernatant of nerve cells derived from AD-iPS cells, the Aβ42/Aβ40 ratio and relative expression amount of FL-APP (the value of FL-APP at 38 days is used as standard).
Figure 17:
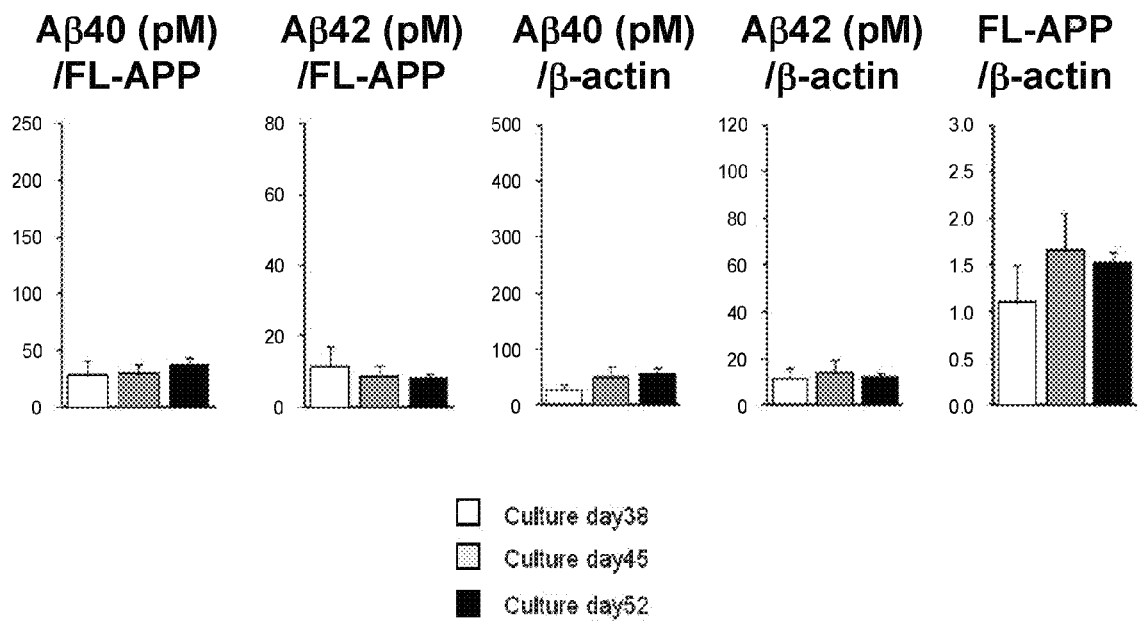
FIG. 17 shows the results of Aβ40/FL-APP ratio, Aβ42/FL-APP ratio, Aβ40/β-actin, Aβ42/β-actin and FL-APP/β-actin. The values of FL-APP and β-actin at 38 days are used as standard.
Figure 18:
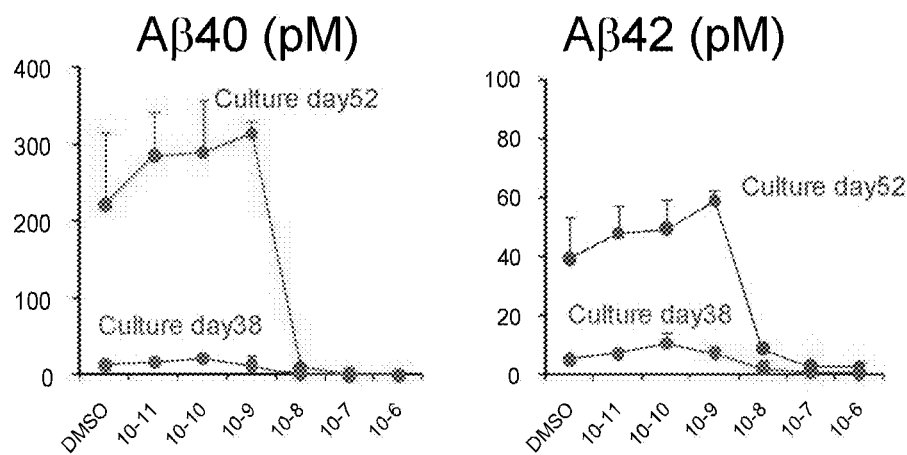
FIG. 18 shows the results of measurement of the contents of Aβ40 (left) and Aβ42 (right) in the culture media of nerve cells derived from AD-iPS cells at 38 and 52 days. The abscissa indicates concentration of γ-secretase inhibitor, Compound E. DMSO means absence of Compound E.

The contents of Aβ40 and Aβ42 in the nerve cells derived from AD-iPS cells were measured with the ELISA method described in Example 1. The concentration of Aβ40 and Aβ42, ratio (Aβ42/Aβ40) and relative amount of FL-APP were shown in FIG. 16. The value of Aβ40 and Aβ42 corrected with amount of FL-APP or β-actin was shown in FIG. 17. These values can be used for assessing for the risk of onset or predicting the age of onset of Alzheimer's disease at 50's.

INDUSTRIAL APPLICABILITY

By using the present invention, the onset of, or the risk of development of, a protein misfolding disease can be diagnosed, and the age of the onset of a protein misfolding disease can be predicted using nerve cells derived from iPS cells of a patient suffering from the protein misfolding disease. Therefore, the present invention is very useful for early treatment or prophylaxis of protein misfolding diseases.

What is claimed is:

1. A method for diagnosing whether a test subject has developed Alzheimer's disease, wherein the test subject has a risk of developing Alzheimer's disease or is suspected of having Alzheimer's disease, said method comprising the steps of:
   (a) establishing iPS cells from somatic cells derived from the test subject;
   (b) inducing differentiation of said iPS cells into nerve cells;
   (c) measuring the amount of a causative protein selected from the amount of Aβ40, the amount of Aβ42, or the ratio of the amount of Aβ42 to that of Aβ40, or the activity or the expression level of an enzyme involved in degradation of the causative protein in said nerve cells, wherein the enzyme is neprilysin;
   (d) comparing said measured value with the amount of the causative protein in control cells, or with the activity or the expression level of the enzyme involved in degradation of the causative protein in control cells, wherein said control cells are nerve cells obtained by inducing differentiation of iPS cells produced from somatic cells derived from a control subject who has not developed Alzheimer's disease at the same age as the test subject, and when the amount of said causative protein in the test subject is higher than that in the control subject, or when the activity or the expression level of neprilysin in the test subject is lower than that in the control subject, it is determined that the test subject has developed Alzheimer's; and
   (e) determining if the subject has developed Alzheimer's disease based upon the comparison in step (d).

2. The method according to claim 1, wherein said subject is human.

3. The method according to claim 1, wherein said differentiation is performed by culturing with media contained B27-supplement and N2-supplement.

4. A method for diagnosing whether a test subject has developed Alzheimer's disease, wherein the test subject has a risk of developing Alzheimer's disease or is suspected of having Alzheimer's disease, said method comprising the steps of:
   (a) establishing iPS cells from somatic cells derived from the test subject;
   (b) inducing differentiation of said iPS cells into nerve cells;
   (c) measuring the amount of a causative protein selected from the amount of Aβ40, the amount of Aβ42, or the ratio of the amount of Aβ42 to that of Aβ40, or the activity or the expression level of an enzyme involved in degradation of the causative protein in said nerve cells, wherein the enzyme is neprilysin;
   (d) comparing said measured value with the amount of the causative protein in control cells, or with the activity or the expression level of the enzyme involved in degradation of the causative protein in control cells, wherein said control cells are nerve cells obtained by inducing differentiation of iPS cells produced from somatic cells derived from a control subject who has already developed Alzheimer's disease at the same age as the test subject, and when the amount of said causative protein in the test subject is higher than or equivalent to that in the control subject, or when the activity or the expression level of neprilysin in the test subject is lower than or equivalent to that in the control subject, it is determined that the test subject has developed Alzheimer's disease; and
   (e) determining if the subject has developed Alzheimer's disease based upon the comparison in step (d).

5. The method according to claim 4, wherein said subject is human.

6. The method according to claim 4, wherein said differentiation is performed by culturing with media contained B27-supplement and N2-supplement.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
tactaccgcg agaacaagca                                              20

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
tcacgaagca cttgttgagg                                              20

<210> SEQ ID NO 3

```
<211> LENGTH: 20
<212> TYPE: DNA
<213> ORGANISM: Artificial sequence
<220> FEATURE:
<223> OTHER INFORMATION: primer

<400> SEQUENCE: 3
cagatgtcca ccacctcaaa                                              20

<210> SEQ ID NO 4
<211> LENGTH: 25
<212> TYPE: DNA
<213> ORGANISM: Artificial sequence
<220> FEATURE:
<223> OTHER INFORMATION: primer

<400> SEQUENCE: 4
ggtcaaataa ttctgttcga gtttt                                        25

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
cctcctccga ctgaagacag                                              20

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
tggtctgggt acaggcctac                                              20

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
gcacaagcag caagatcaaa                                              20

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
caaccagcaa atgcttctca                                              20

<210> SEQ ID NO 9
<211> LENGTH: 20
<212> TYPE: DNA
<213> ORGANISM: Artificial sequence
<220> FEATURE:
<223> OTHER INFORMATION: primer
```

-continued

<400> SEQUENCE: 9
atcctcagcc ccttttgttt                                                    20

<210> SEQ ID NO 10
<211> LENGTH: 20
<212> TYPE: DNA
<213> ORGANISM: Artificial sequence
<220> FEATURE:
<223> OTHER INFORMATION: primer

<400> SEQUENCE: 10
gccgttgttc ctgaattgtt                                                    20

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
aacgaggcct cttctcacaa                                                    20

<210> SEQ ID NO 12
<211> LENGTH: 20
<212> TYPE: DNA
<213> ORGANISM: Artificial sequence
<220> FEATURE:
<223> OTHER INFORMATION: primer

<400> SEQUENCE: 12
ggcctgaaga gatgtccaaa                                                    20

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
ggttgagagg gacaatctgg                                                    20

<210> SEQ ID NO 14
<211> LENGTH: 19
<212> TYPE: DNA
<213> ORGANISM: Artificial sequence
<220> FEATURE:
<223> OTHER INFORMATION: primer

<400> SEQUENCE: 14
aggttgttct cggcttcca                                                     19

<210> SEQ ID NO 15
<211> LENGTH: 20
<212> TYPE: DNA
<213> ORGANISM: Artificial sequence
<220> FEATURE:
<223> OTHER INFORMATION: primer

<400> SEQUENCE: 15
gacggaaggg atcacatcat                                                    20

<210> SEQ ID NO 16
<211> LENGTH: 19
<212> TYPE: DNA
<213> ORGANISM: Artificial sequence
<220> FEATURE:
<223> OTHER INFORMATION: primer

<400> SEQUENCE: 16
ctggtggtca ccaatgagc                                                  19

<210> SEQ ID NO 17
<211> LENGTH: 19
<212> TYPE: DNA
<213> ORGANISM: Artificial sequence
<220> FEATURE:
<223> OTHER INFORMATION: primer

<400> SEQUENCE: 17
gcttcgcgtt atcatcctg                                                  19

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
ccaagatgaa ccagaccaca                                                 20

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
aagtggggca tcctccttat                                                 20

<210> SEQ ID NO 20
<211> LENGTH: 21
<212> TYPE: DNA
<213> ORGANISM: Artificial sequence
<220> FEATURE:
<223> OTHER INFORMATION: primer

<400> SEQUENCE: 20
tgacgccagg tttattccat a                                               21

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
atgctgtggg gaggctttat                                                 20

<210> SEQ ID NO 22
<211> LENGTH: 20
<212> TYPE: DNA
<213> ORGANISM: Artificial sequence
<220> FEATURE:

-continued

```
<223> OTHER INFORMATION: primer

<400> SEQUENCE: 22
ctcggatctg tgcaatcaaa                                                    20
```